US009430617B2

(12) United States Patent
Brust et al.

(10) Patent No.: US 9,430,617 B2
(45) Date of Patent: Aug. 30, 2016

(54) CONTENT SUGGESTION ENGINE

(71) Applicants: Thomas Edwin Brust, White Bear Lake, MN (US); Phillip Kennedy, Eagan, MN (US); Jamal Khan, Redding, CT (US); Jay W. Johnson, Sarasota, FL (US); Tom Waddell, New Brighton, MN (US)

(72) Inventors: Thomas Edwin Brust, White Bear Lake, MN (US); Phillip Kennedy, Eagan, MN (US); Jamal Khan, Redding, CT (US); Jay W. Johnson, Sarasota, FL (US); Tom Waddell, New Brighton, MN (US)

(73) Assignee: Wellclub, LLC, Saint Paul, MN (US)

( * ) Notice: Subject to any disclaimer, the term of this patent is extended or adjusted under 35 U.S.C. 154(b) by 0 days.

(21) Appl. No.: 14/713,276

(22) Filed: May 15, 2015

(65) Prior Publication Data

US 2015/0356261 A1    Dec. 10, 2015

Related U.S. Application Data

(63) Continuation of application No. 13/772,697, filed on Feb. 21, 2013, now Pat. No. 9,037,578.

(60) Provisional application No. 61/732,676, filed on Dec. 3, 2012.

(51) Int. Cl.
| | |
|---|---|
| *G06F 17/00* | (2006.01) |
| *G06F 19/00* | (2011.01) |
| *G06F 17/30* | (2006.01) |
| *G06F 3/0481* | (2013.01) |
| *G06Q 10/10* | (2012.01) |

(52) U.S. Cl.
CPC ........... *G06F 19/345* (2013.01); *G06F 3/0481* (2013.01); *G06F 17/30386* (2013.01); *G06F 17/30554* (2013.01); *G06F 17/30598* (2013.01); *G06Q 10/10* (2013.01); *G06F 19/363* (2013.01)

(58) Field of Classification Search
CPC .......... G06F 19/3418; G06F 19/3481; G06F 19/322; G06F 19/3456; G06F 19/363; G06F 19/3406
See application file for complete search history.

(56) References Cited

U.S. PATENT DOCUMENTS

| | | | |
|---|---|---|---|
| 4,853,854 A | 8/1989 | Behar et al. | |
| 5,251,126 A | 10/1993 | Kahn et al. | |
| 5,596,994 A | 1/1997 | Bro | |
| 5,933,136 A | 8/1999 | Brown | |
| 6,039,688 A | 3/2000 | Douglas et al. | |

(Continued)

OTHER PUBLICATIONS

"U.S. Appl. No. 13/772,405, Examiner Interview Summary mailed Apr. 21, 2015", 3 pgs.

(Continued)

*Primary Examiner* — Truong Vo
(74) *Attorney, Agent, or Firm* — Schwegman Lundberg & Woessner, P.A.

(57) ABSTRACT

Systems and methods for content selection and processing in an information system are described herein. In one example, a content suggestion engine operates to select, suggest, or recommend content to human users. The selection of content may be suited to a goal or set of goals set by a human user (for example, content recommendations used to assist the human user with achieving a personal health goal). The content suggestion engine may evaluate information to help determine the appropriateness of the content suggestions, considering factors such as a psychological profile, medical conditions, lifestyle, demographics, and goals. The content may be further filtered and weighted to select a subset of content and suggested actions most relevant to the human user.

28 Claims, 10 Drawing Sheets

(56) References Cited

U.S. PATENT DOCUMENTS

| | | |
|---|---|---|
| 6,059,724 A | 5/2000 | Campell et al. |
| 6,101,478 A | 8/2000 | Brown |
| 6,144,837 A | 11/2000 | Quy |
| 6,240,394 B1 | 5/2001 | Uecker et al. |
| 6,294,999 B1 | 9/2001 | Yarin et al. |
| 6,381,577 B1 | 4/2002 | Brown |
| 6,547,727 B1 | 4/2003 | Hashiguchi et al. |
| 6,697,783 B1 | 2/2004 | Brinkman et al. |
| 7,216,084 B2 | 5/2007 | Brinkman et al. |
| 7,223,235 B2 | 5/2007 | Brown |
| 7,258,666 B2 | 8/2007 | Brown |
| 7,261,690 B2 | 8/2007 | Teller et al. |
| 7,287,031 B1 | 10/2007 | Karpf et al. |
| 7,297,109 B2 | 11/2007 | Brown |
| 7,299,192 B2 | 11/2007 | Luttrell |
| 7,302,398 B2 | 11/2007 | Ban et al. |
| 7,376,700 B1 | 5/2008 | Clark |
| 7,395,216 B2 | 7/2008 | Rosenfeld et al. |
| 7,412,511 B2 | 8/2008 | Curry |
| 7,478,129 B1 | 1/2009 | Chemtob et al. |
| 7,493,264 B1 | 2/2009 | Kelly et al. |
| 7,555,436 B2 | 6/2009 | Brown |
| 7,584,108 B2 | 9/2009 | Brown |
| 7,590,549 B2 | 9/2009 | Brown |
| 7,636,667 B2 | 12/2009 | Brown |
| 7,647,234 B1 | 1/2010 | Ruderman et al. |
| 7,653,556 B2 | 1/2010 | Rovinelli et al. |
| 7,684,999 B2 | 3/2010 | Brown |
| 7,685,000 B1 | 3/2010 | Petit et al. |
| 7,689,437 B1 | 3/2010 | Teller et al. |
| 7,689,440 B2 | 3/2010 | Brown |
| 7,720,855 B2 | 5/2010 | Brown |
| 7,739,124 B1 | 6/2010 | Walker et al. |
| 7,752,056 B2 | 7/2010 | Brown |
| 7,756,722 B2 | 7/2010 | Levine et al. |
| 7,765,112 B2 | 7/2010 | Brown |
| 7,769,600 B2 | 8/2010 | Iliff |
| 7,778,845 B2 | 8/2010 | Brown |
| 7,788,113 B2 | 8/2010 | Fuhrman et al. |
| 7,801,745 B2 | 9/2010 | Walker et al. |
| 7,809,584 B2 | 10/2010 | Morag et al. |
| 7,822,621 B1 | 10/2010 | Chappel |
| 7,822,625 B2 | 10/2010 | Brown |
| 7,827,039 B2 | 11/2010 | Butcher et al. |
| 7,827,040 B2 | 11/2010 | Brown |
| 7,827,042 B2 | 11/2010 | Jung et al. |
| 7,840,420 B2 | 11/2010 | Brown |
| 7,862,506 B2 | 1/2011 | Brown |
| 7,867,165 B2 | 1/2011 | Brown |
| 7,869,852 B2 | 1/2011 | Brown |
| 7,870,249 B2 | 1/2011 | Brown |
| 7,871,376 B2 | 1/2011 | Brown |
| 7,877,274 B2 | 1/2011 | Brown |
| 7,877,276 B2 | 1/2011 | Brown |
| 7,890,346 B2 | 2/2011 | Padron et al. |
| 7,904,530 B2 | 3/2011 | Partridge et al. |
| 7,921,186 B2 | 4/2011 | Brown |
| 7,925,522 B2 | 4/2011 | Brown |
| 7,941,323 B2 | 5/2011 | Brown |
| 7,941,326 B2 | 5/2011 | Brown |
| 7,941,327 B2 | 5/2011 | Brown |
| 7,944,342 B2 | 5/2011 | Sekura |
| 7,944,448 B2 | 5/2011 | Iwamura et al. |
| 7,945,461 B2 | 5/2011 | Sekura |
| 7,955,219 B2 | 6/2011 | Birrell et al. |
| 7,970,620 B2 | 6/2011 | Brown |
| 7,972,247 B2 | 7/2011 | Daikeler et al. |
| 7,979,284 B2 | 7/2011 | Brown |
| 7,985,164 B2 | 7/2011 | Ashby |
| 7,993,267 B2 | 8/2011 | Iliff |
| 8,013,736 B2 | 9/2011 | Derrick et al. |
| 8,015,025 B2 | 9/2011 | Brown |
| 8,015,030 B2 | 9/2011 | Brown |
| 8,015,033 B2 | 9/2011 | Brown |
| 8,015,138 B2 | 9/2011 | Illiff |
| 8,019,618 B2 | 9/2011 | Brown |
| 8,024,201 B2 | 9/2011 | Brown |
| 8,032,399 B2 | 10/2011 | Brown |
| 8,034,294 B1 | 10/2011 | Goldberg |
| 8,036,912 B2 | 10/2011 | Jensen et al. |
| 8,038,577 B2 | 10/2011 | McIntosh |
| 8,055,516 B2 | 11/2011 | Iliff |
| 8,066,514 B2 | 11/2011 | Clarke |
| 8,069,131 B1 | 11/2011 | Luechtefeld et al. |
| 8,073,707 B2 | 12/2011 | Teller et al. |
| 8,075,451 B2 | 12/2011 | Dugan |
| 8,078,492 B2 | 12/2011 | Brown et al. |
| 8,095,522 B2 | 1/2012 | Welti et al. |
| 8,100,757 B2 | 1/2012 | Melendez |
| 8,108,226 B2 | 1/2012 | Barrett |
| 8,109,874 B2 | 2/2012 | Kong et al. |
| 8,131,570 B2 | 3/2012 | Levin et al. |
| 8,140,663 B2 | 3/2012 | Brown |
| 8,160,901 B2 | 4/2012 | Heywood et al. |
| 8,165,893 B1 | 4/2012 | Goldberg et al. |
| 8,170,807 B2 | 5/2012 | Barnett et al. |
| 8,180,592 B2 | 5/2012 | Yuen et al. |
| 8,182,267 B2 | 5/2012 | Katz et al. |
| 8,182,424 B2 | 5/2012 | Heckerman |
| 8,202,202 B2 | 6/2012 | McGlynn et al. |
| 8,234,127 B2 | 7/2012 | Naik et al. |
| 8,277,377 B2 | 10/2012 | Quy |
| 9,037,578 B2 | 5/2015 | Brust et al. |
| 9,110,958 B2 | 8/2015 | Brust et al. |
| 2001/0027403 A1 | 10/2001 | Peterson et al. |
| 2001/0039503 A1 | 11/2001 | Chan et al. |
| 2002/0026333 A1 | 2/2002 | Endou |
| 2002/0055857 A1 | 5/2002 | Mault |
| 2002/0055859 A1 | 5/2002 | Goodman et al. |
| 2002/0072932 A1 | 6/2002 | Swamy |
| 2002/0087358 A1 | 7/2002 | Gilbert |
| 2002/0128861 A1 | 9/2002 | Lau et al. |
| 2002/0133377 A1 | 9/2002 | Brown |
| 2002/0183598 A1 | 12/2002 | Teraura et al. |
| 2002/0184056 A1 | 12/2002 | Tsuboi |
| 2003/0014279 A1 | 1/2003 | Roman et al. |
| 2003/0061065 A1 | 3/2003 | Keeley |
| 2003/0061215 A1 | 3/2003 | Messina |
| 2003/0065561 A1 | 4/2003 | Brown et al. |
| 2003/0101076 A1 | 5/2003 | Zaleski |
| 2003/0182161 A1 | 9/2003 | Vanderlei et al. |
| 2004/0131997 A1 | 7/2004 | McGuire et al. |
| 2004/0176666 A1 | 9/2004 | Chait |
| 2004/0215491 A1 | 10/2004 | Clark et al. |
| 2004/0242973 A1 | 12/2004 | Tanabe et al. |
| 2004/0243443 A1 | 12/2004 | Asano et al. |
| 2005/0095628 A1 | 5/2005 | Krempin et al. |
| 2005/0113650 A1 | 5/2005 | Pacione et al. |
| 2005/0117527 A1 | 6/2005 | Williams et al. |
| 2005/0240434 A1 | 10/2005 | Wooten et al. |
| 2005/0240438 A1 | 10/2005 | Day |
| 2005/0240444 A1 | 10/2005 | Wooten et al. |
| 2005/0283385 A1 | 12/2005 | Hunkeler et al. |
| 2005/0283386 A1 | 12/2005 | Powers et al. |
| 2006/0004611 A1 | 1/2006 | Brown |
| 2006/0010014 A1 | 1/2006 | Brown |
| 2006/0026036 A1 | 2/2006 | Mahmood |
| 2006/0064322 A1 | 3/2006 | Mascarenhas et al. |
| 2006/0189853 A1 | 8/2006 | Brown |
| 2006/0224416 A1 | 10/2006 | Lloyd et al. |
| 2006/0235722 A1 | 10/2006 | Brown |
| 2007/0005395 A1 | 1/2007 | Singh |
| 2007/0016446 A1 | 1/2007 | Brown |
| 2007/0021984 A1 | 1/2007 | Brown |
| 2007/0055549 A1 | 3/2007 | Moore et al. |
| 2007/0061167 A1 | 3/2007 | Brown |
| 2007/0072156 A1 | 3/2007 | Kaufman et al. |
| 2007/0100595 A1 | 5/2007 | Earles et al. |
| 2007/0190501 A1 | 8/2007 | Brown |
| 2007/0260511 A1 | 11/2007 | Bender |
| 2007/0282842 A1 | 12/2007 | Messinaq |
| 2008/0004902 A1 | 1/2008 | Leong-fern et al. |
| 2008/0103814 A1 | 5/2008 | Fabius et al. |
| 2008/0103855 A1 | 5/2008 | Hernandez et al. |

(56) References Cited

U.S. PATENT DOCUMENTS

| | | |
|---|---|---|
| 2008/0124689 A1 | 5/2008 | Williams et al. |
| 2008/0126276 A1 | 5/2008 | Williams et al. |
| 2008/0126277 A1 | 5/2008 | Williams et al. |
| 2008/0140449 A1 | 6/2008 | Hayes |
| 2008/0162352 A1 | 7/2008 | Gizewski |
| 2008/0168032 A1 | 7/2008 | Criou et al. |
| 2008/0172246 A1 | 7/2008 | Larkin |
| 2008/0183757 A1 | 7/2008 | Dorogusker et al. |
| 2008/0243543 A1 | 10/2008 | Jung |
| 2008/0287748 A1 | 11/2008 | Sapounas et al. |
| 2008/0318678 A1 | 12/2008 | Stivoric et al. |
| 2009/0005009 A1 | 1/2009 | Marsili |
| 2009/0012988 A1 | 1/2009 | Brown |
| 2009/0030732 A1 | 1/2009 | Jung |
| 2009/0043613 A1 | 2/2009 | Jung et al. |
| 2009/0069643 A1 | 3/2009 | Quy |
| 2009/0070141 A1 | 3/2009 | Jolley |
| 2009/0112617 A1 | 4/2009 | Jung et al. |
| 2009/0118593 A1 | 5/2009 | Jung |
| 2009/0119154 A1 | 5/2009 | Jung |
| 2009/0131089 A1 | 5/2009 | Micali et al. |
| 2009/0132275 A1 | 5/2009 | Jung et al. |
| 2009/0193082 A1 | 7/2009 | Brown |
| 2009/0199230 A1 | 8/2009 | Kumar et al. |
| 2009/0312668 A1 | 12/2009 | Leuthardt et al. |
| 2010/0010829 A1 | 1/2010 | Moore et al. |
| 2010/0063833 A1 | 3/2010 | Mahoney |
| 2010/0150384 A1 | 6/2010 | Waldmann |
| 2010/0235776 A1 | 9/2010 | Brown |
| 2010/0250497 A1 | 9/2010 | Redlich et al. |
| 2011/0152635 A1 | 6/2011 | Morris et al. |
| 2011/0172497 A1 | 7/2011 | Ruby et al. |
| 2011/0209037 A1 | 8/2011 | Yoon et al. |
| 2011/0276451 A1 | 11/2011 | Busse |
| 2012/0011139 A1 | 1/2012 | Drissi et al. |
| 2012/0149972 A1 | 6/2012 | Moore |
| 2012/0221345 A1 | 8/2012 | Mcclure et al. |
| 2012/0272278 A1 | 10/2012 | Bedi |
| 2013/0124218 A1 | 5/2013 | Masloski et al. |
| 2014/0100955 A1 | 4/2014 | Osotio et al. |
| 2014/0156308 A1 | 6/2014 | Ohnemus et al. |
| 2014/0156645 A1 | 6/2014 | Brust et al. |
| 2014/0156646 A1 | 6/2014 | Brust et al. |
| 2014/0156676 A1 | 6/2014 | Brust et al. |
| 2014/0157171 A1 | 6/2014 | Brust et al. |

OTHER PUBLICATIONS

"U.S. Appl. No. 13/772,405, Non Final Office Action mailed Jan. 7, 2015", 22 pgs.

"U.S. Appl. No. 13/772,405, Response filed May, 7, 2015 to Non Final Office Action mailed Jan. 7, 2015", 22 pgs.

"U.S. Appl. No. 13/772,697, Examiner Interview Summary mailed Dec. 17, 2014", 3 pgs.

"U.S. Appl. No. 13/772,697, Non Final Office Action mailed Sep. 3, 2014", 12 pgs.

"U.S. Appl. No. 13/772,697, Notice of Allowance mailed Jan. 20, 2015", 7 pgs.

"U.S. Appl. No. 13/772,697, Response filed Dec. 23, 2014 to Non Final Office Action mailed Sep. 3, 2014", 16 pgs.

"U.S. Appl. No. 13/801,048, Examiner Interview Summary mailed Mar. 27, 2015", 3 pgs.

"U.S. Appl. No. 13/801,048, Non Final Office Action mailed Nov. 25, 2014", 8 pgs.

"U.S. Appl. No. 13/801,048, Response filed Mar. 25, 2015 to Non Final Office Action mailed Nov. 25, 2014", 15 pgs.

"U.S. Appl. No. 13/801,315, Non Final Office Action mailed Apr. 6, 2015", 20 pgs.

"Lift", Powered by Tumblr, [Online]. Retrieved from the Internet: <URL: https://web.archive.org/web/20121116235453/http:/blog.lift.do/, (Nov. 16, 2012), 17 pgs.

"U.S. Appl. No. 13/772,405, Final Office Action mailed Jul. 9, 2015", 23 pgs.

"U.S. Appl. No. 13/772,405, Notice of Allowance mailed Aug. 28, 2015", 8 pgs.

"U.S. Appl. No. 13/772,405,Response filed Aug. 10, 2015 to Final Office Action mailed Jul. 9, 2015", 16 pgs.

"U.S. Appl. No. 13/801,048, Notice of Allowance mailed Jun. 5, 2015", 7 pgs.

"U.S. Appl. No. 13/801,315, Notice of Allowance mailed Sep. 15, 2015", 10 pgs.

"U.S. Appl. No. 13/801,315, Response filed Jul. 1, 2015 to Non Final Office Action mailed Apr. 6, 2015", 12 pgs.

| ACTION STATEMENT | DIFFICULTY | DURATION | BEHAVIOR | RESTRICTIONS |
|---|---|---|---|---|
| WALK IN THE PARK | LOW | 15 MIN | SOCIAL | MOBILITY |
| EAT OATMEAL BREAKFAST | LOW | 10 MIN | | DIET |
| 30 MINUTE ROLLERBLADE | MEDIUM | 30 MIN | SOCIAL | HIGH MOBILITY |
| EAT WHOLE GRAIN CEREAL | LOW | 10 MIN | | DIET |

CONTENT SUGGESTION ENGINE

CROSS-REFERENCE TO RELATED APPLICATIONS

This application is a continuation of and claims priority to U.S. patent application Ser. No. 13/772,697, titled "CONTENT SUGGESTION ENGINE", filed Feb. 21, 2013, which claims priority under 35 U.S.C. §119(e) to U.S. Provisional Patent Application Ser. No. 61/732,676, titled "CONTENT SUGGESTION ENGINE", filed Dec. 3, 2012, which are incorporated herein by reference in their entirety. This application includes subject matter related to pending U.S. patent application Ser. No. 13/772,405, titled "GOAL-BASED CONTENT SELECTION AND DELIVERY", filed Feb. 21, 2013; Ser. No. 13/801,048, titled "EXPERT-BASED CONTENT AND COACHING PLATFORM", filed Mar. 13, 2013; and Ser. No. 13/801,315, titled "METHODOLOGY FOR BUILDING AND TAGGING RELEVANT CONTENT", filed Mar. 13, 2013; the entireties of which are hereby incorporated by reference.

TECHNICAL FIELD

Embodiments pertain to techniques and systems for content selection and management. Some embodiments relate to data-driven operations in a content suggestion engine to select, suggest, or recommend content for output to human subjects.

BACKGROUND

Various data services select or recommend content for display to users. For example, in the self-help setting, a variety of existing data services provide tips, recommendations, and focused content to assist a subject human user with goal-based outcomes such as weight loss, smoking cessation, medical therapy, exercise goals, and the like. Some of these data services provide recommended content to a user in response to user-indicated preferences, user-indicated activity history, or manual user requests for content. Other data services rely on an expert human user to determine which content is most appropriate for delivery to the subject human user to achieve a certain outcome.

To the extent that existing data services provide automated recommendations or selections of content, the timing, delivery, and substance of the content from these data services is determined by complex predetermined rules and attributes, or other selections influenced by manual human intervention. For example, recommendations may be hard-coded in a content delivery system to deliver suggestive content in a particular fashion responsive to some detected condition. Existing systems and techniques do not provide real-time recommendations and content selections without extensive programming or oversight.

DETAILED DESCRIPTION

Figure 1:
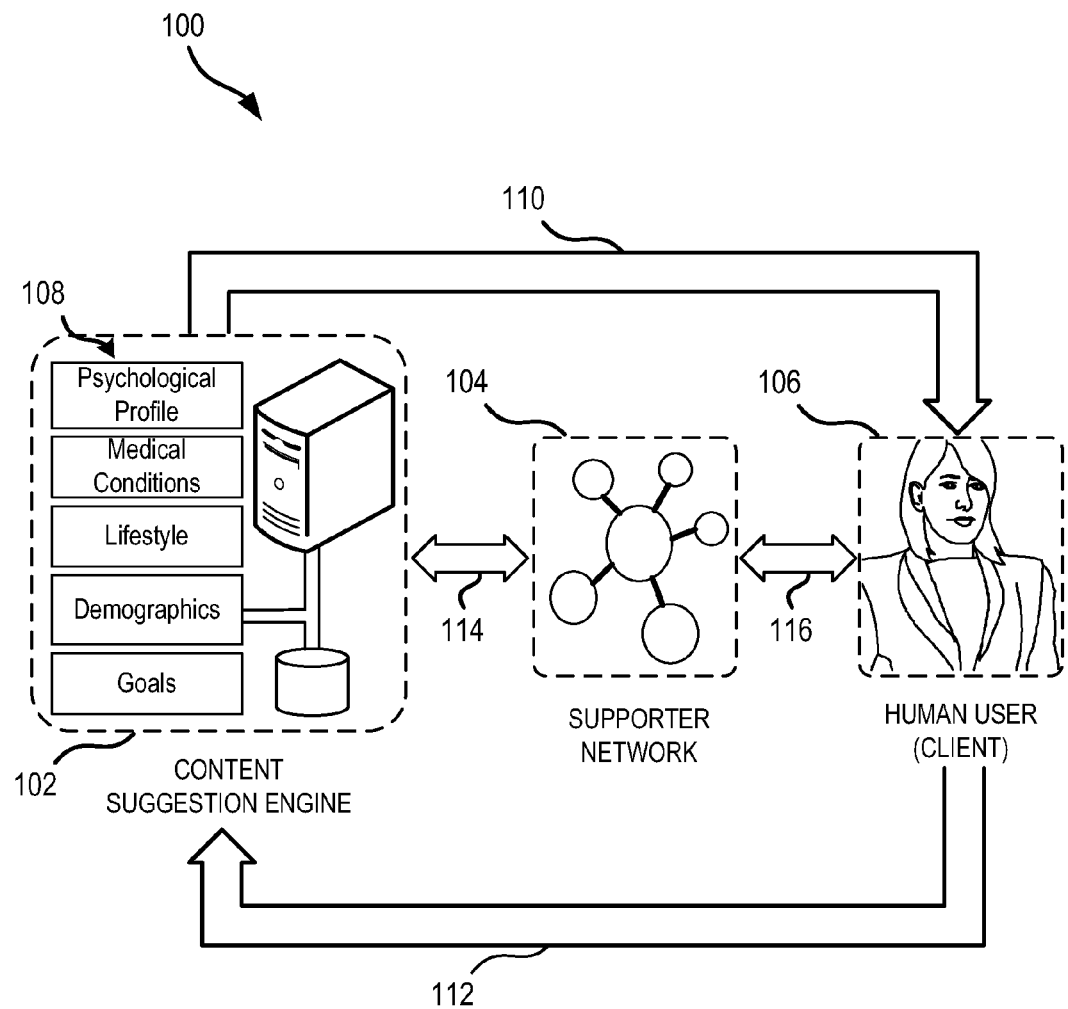
FIG. 1 illustrates an information flow diagram of interaction with an example information system and a content suggestion engine, according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The present disclosure illustrates techniques and configurations to enable the filtering of content and related content delivery actions in order to generate content relevant for human activities to accomplish some predetermined or ongoing goal or set of goals. The type, substance, and delivery of the content serve to provide a human user with motivating suggestions, encouragement, and positive reinforcement towards attaining this goal or set of goals.

The computing systems and platforms encompassed by the present disclosure include a mobile or web-based social networking information service, interacting with a suggestion engine, that is used to motivate a human user to change behavior (such as healthy lifestyle choices and activities that are likely to lead to a positive health outcome) through a persistent intelligent coaching model. The information service can provide intelligent decision making and reinforcement of certain content and content actions in order to facilitate encouragement or motivation that increases the likelihood of change in human behavior to achieve the goal. In particular, the information service focuses on encouraging a human user to complete a series of discrete, separate actions or activities (to achieve small goals) that in combination will help achieve a larger overall goal. For example, in a weight loss setting, this can include a series of tens, hundreds, or thousands of discrete diet and exercise actions that in combination will help the human user achieve a weight loss goal.

In conjunction with operations of the suggestion engine, the information service can adapt to learn a user's behavior patterns and offer personalized, relevant, or timely suggestions, motivations, or other directed content to help the human user achieve the goal. The information service also can enable peer and professional support for a human user by creating and maintaining human connections relevant to the goal, such as through establishing social networking connections and social networking interactions customized to the goal. As the social network or the behaviors of the human user change, the information service can adapt to alter the actions, motivations, or other directed content to remain relevant, personal, or timely to the human user. In this fashion, the information service is intended to cause behavior changes of the human users, through promotion of actions to achieve the user's goals with social encouragement by friends, family, or team members (supporters), personal motivations reinforced with reminders, or new structures in their living environment, such as can be helpful in altering habits to achieve the goal.

The information service can include various applications and corresponding user interfaces to be viewed by the human user and supporters of the human user to encourage beneficial interactions between the human user and the supporters. These interactions, which may be driven by suggested content and suggested content delivery types or timings, are used to cause activities that lead to the intended behavior change(s) in a human user. Accordingly, the content suggestion engine acts in a larger environment of an "intelligent" information system that provides appropriate messages and content selections to the human user and supporters at the right time.

FIG. 1 illustrates an information flow diagram of interaction with an example information system 100 configured for providing content (e.g., motivations, recommendations, suggestions, facts, or other relevant material) to human users. The information system 100 can include a suggestion engine 102, participation from a supporter network 104 of various human or automated users, and participation from a subject human user (further referred to herein as a "client") 106.

The suggestion engine 102 can be configured to make decisions to deliver relevant content dynamically (e.g., at the proper time, in the proper context, and with the proper communication medium) using data conditions 108 maintained for the client 106. The data conditions 108 maintained for the client 106 may include information such as: one or more goals of the client; demographic information such as gender, age, and familial information; medical information such as medical conditions, medical history, and medical or physical restrictions; a psychological profile and other psychological information such as personality type, daily routines or habits, emotional status, likes and dislikes; and available external devices (e.g., smart phone or smart phone applications, smart weight scales, smart televisions, video game systems, etc.); client desired coaching programs and models (e.g., diet style, exercise focus, or mental health); and information relevant to discrete activities, such as present or scheduled locations of the client, and time to accomplish activities; and information relevant to the goal, such as time to achieve the goal, difficulty of achieving the goal; and like information for conditions relevant to the human user, supporters of the human user, or the overall goal.

The specific content selection operations of the suggestion engine 102 are directed to change the behavior of the client 106, such as to help the client 106 achieve a defined or derived goal with a series of content messages that are intended to invoke action by suggested activities and events. Delivery of the content may be provided directly from the suggestion engine 102 to the client 106 with a content delivery flow 110. With the content delivery flow 110, the suggestion engine 102 can query the client 106, periodically or randomly, to gain information and feedback that can affect what content is delivered to the client 106. Responses by the client 106 may be provided back to the content suggestion engine 102 through a content feedback flow 112 to indicate the results of such querying or feedback.

The suggestion engine 102 may also provide indirect content delivery flows 114, 116 through a supporter network 104, to enable the supporter network 104 to provide content to the client 106 at appropriate times. Specifically, the suggestion engine 102 can indirectly provide content selections to the user using an indirect content delivery flow 114, and orchestrate resources of the supporter network 104 by engaging influential persons (e.g., family, friends, or others that influence the client 106) to forward or deliver the content to the client 106.

The supporter network 104 may also facilitate interaction between the client 106 and healthcare providers or other professionals (e.g., nutritionists, personal trainers, psychologists, or behavior coaches, among others). Such interaction from the supporter network 104 may be used to proactively guide personalized and critically timed suggestions (e.g., such as by sending a message that encourages a specific activity), or persistently coaching, guiding, motivating, or focusing the client 106 to complete actions to achieve his or her goal.

Additionally, members of the supporter network 104 may generate and provide suggestions back to the content suggestion engine 102, directly or with crowd sourcing-type mechanisms distributed among a plurality of persons. For example, a supporter can directly author suggestions that are sent to the human user, or edit, modify, or unify suggestions with slight modifications for the client 106 using feedback from other human users. Based on the effectiveness of the content created by the supporter network 104, a pool of suggestions may be created.

Thus, the supporter network 104 may be used to generate or forward content selected by the content suggestion engine 102, using indirect content delivery flow 116. For example, the suggestion engine 102 may provide a supporter of the supporter network 104 with pre-formatted action content that can be sent directly from the supporter to the client 106 using a recognized communication medium, such as by forwarding and customizing a text message, an email message, a social network message, and the like. Suggestions directly received from members of the supporter network 104 are more likely to reduce barriers or excuses of inaction, and empower the client 106 to perform an action or actions that will help achieve their goals. Feedback may also be provided back to members of the supporter network 104 from the client 106 (such as a confirmation that the client 106 performed the activity, a message that the client 106 enjoyed the suggestion, a message asking for support to perform the activity, and the like).

The suggestion engine 102 can communicate with the supporter network 104 and the client 106, such as to obtain information about the client 106 or provide messages to the client 106 or to the supporter network 104. The supporter network 104 can personalize the message and send the message to the client 106, such as shown in FIG. 1. By having the client 106 receive the message from the supporter network 104, the message can have more impact, and potentially be more motivating, than if it came directly from the suggestion engine 102.

Suggestion Content Types and Delivery

Appropriate messages, multimedia, and other content delivered to the client 106 from or on behalf of the information system are referred to herein as "suggestion content," as the content can be selected and produced by the content suggestion engine 102. Suggestion content can include content from one or more messages that the client 106 and supporters 104 receive that are collectively intended to cause human attention and persuade the client 106 to perform some action. The suggestion content can be tailored and customized to be appropriate to the client 106, time, and individual intended actions. The suggestion content can include a variety of formats, such as content that indicates greetings, actions, motivations, prompts, reminders, and rewards.

Described herein are types of suggestion content, ways that suggestion content can be aggregated, and techniques for creating and delivering the suggestion content. Further described herein are system, apparatus, and device configurations to implement the suggestion engine that can enable a particular selection of suggestion content to be sent to the supporter network 104 or client 106. As used herein, suggestion content can include content delivered to the client 106 intended to cause an action related to an ultimate goal. Suggested action content sent to the client 106, as further described herein, may be constructed from content that includes an action statement 306, and a pre statement 304 or a post statement 308 (as further described below with reference to FIG. 3A).

As used herein, motivational content is a specific subset of suggestion content that is intended to improve the likelihood of the client 106 performing a suggested action by appealing to some human interest. Motivational content may be embodied by: various prompts that include a request for a response from the client 106 or supporter network 104; reminders that include a statement that reminds the client 106 or a supporter from the supporter network 104 that an action is due on their part; rewards that include statements provided to the client 106 or supporter that are congratulatory or explain something being given to the client 106 or supporter; or supporter messages that include content specifically intended for the supporter.

Content provided by the information system may be stored and maintained in structured and unstructured form. Unstructured content can include suggestion content not yet edited, tagged, or final reviewed; whereas structured content can include content that has been edited, tagged, and reviewed, and is ready for use by the suggestion engine 102 (as further illustrated with reference below to FIG. 2).

Content can be tagged for use in defined retrieval operations. Such tagging can include a psychological assessment matching. A client 106 can be asked to take assessments for engagement, receptivity, or social style. The content can be tagged in such a way that the system matches the client 106 with the style of the content suited for them. This can "personalize" the interactions between the system and the client 106, such as to provide a more effective or engaging environment. The system can provide content for each of eating, movement (e.g., actions to physically accomplish), and self-view. The tags can provide and store this information.

As further discussed herein, the tagging of data can include "behavior change" tagging. A current behavior change theory promotes a combination of "sources of behavior change" that promote a higher probability of changing people's behavior. These sources of behavior change include items that improve an individual's intrinsic motivation or extrinsic motivation and aptitude, group factors and power to cause behavior change, and environmental factors and power to cause behavior change. Presenting suggestions that fit in multiple behavior change areas can be more effective than presenting suggestions in just one or a few of the areas. Additionally, the client 106 can fill out a lifestyle questionnaire, which determines, such as by using Boolean logic, different "problems" that the client 106 may have. Content can be tagged with these problems, such as to tag content that relates to the problem. The client 106 can work on the problem by choosing specific suggestions or playlists of suggestions tagged with that problem.

In one example use of a suggestion engine 102, the client 106 is the person that the information system is intended to help; the supporter network 104 can include one of the persons providing aid to the client 106—this person could be a team member, friend, family member, or paid supporter such as personal trainer, among others. Thus, overall users of the suggestion engine 102 can include any person using the information service (and accompanying applications, websites, and services), including the client 106, supporters in the supporter network 104, an administrator, and the like.

The information system 100 facilitates interaction with the client 106 and supporters in the supporter network 104, such as encouraging clients and supporters to interact in the social network, to accompany several types of content. Content can be created that gives clients and supporters specific actions to perform, and this content can be delivered in a way that encourages the supporter or client 106 to perform the action. The content can be designed to be delivered to the client 106 either directly or through the supporter. A plurality of action statements (further described with reference to action statement 302 depicted in FIG. 3A) providing respective suggested actions can be presented to the client 106 for participation. Other types of content can be used to increase the probability of the client 106 performing the suggested actions.

Figure 2:
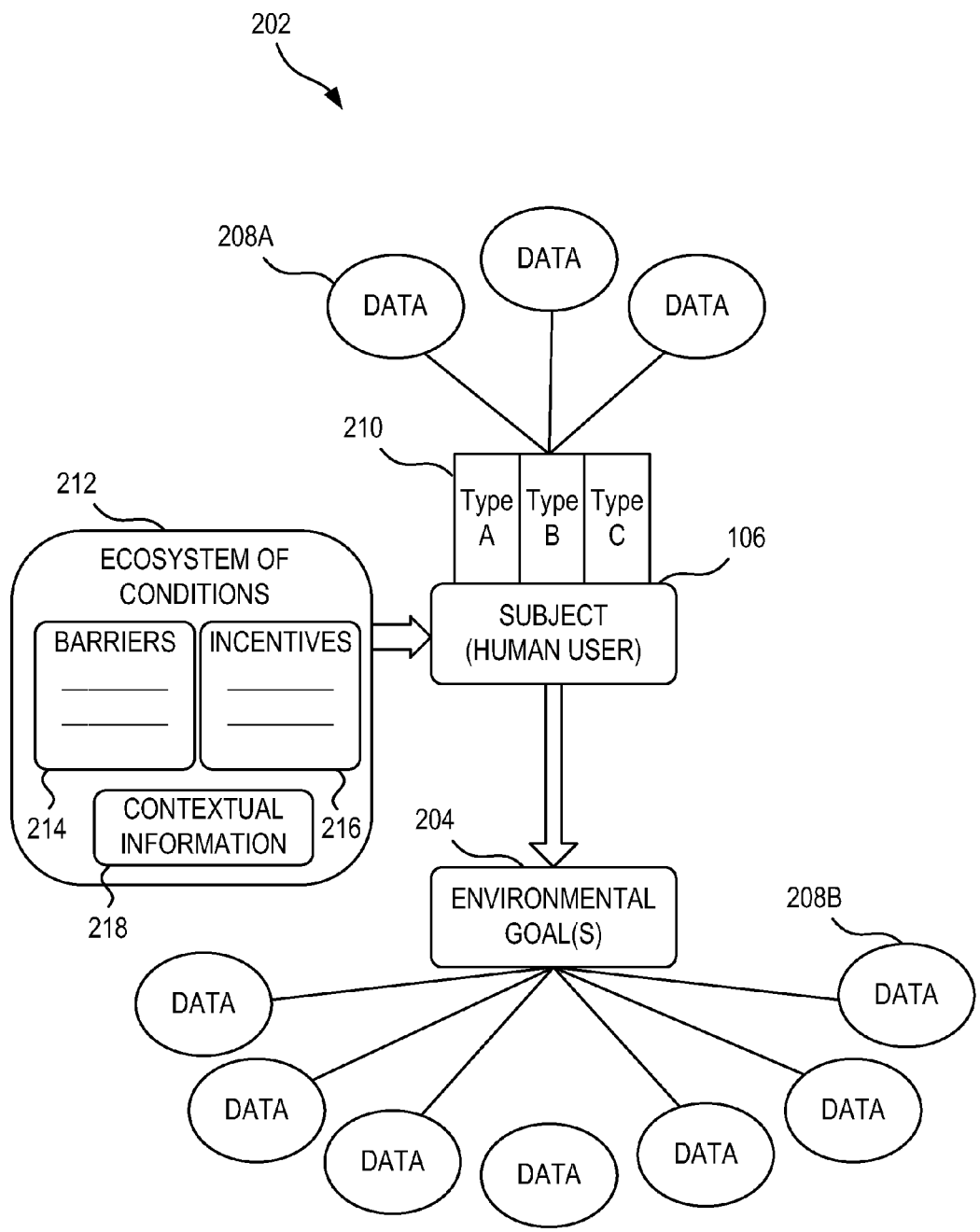
FIG. 2 illustrates an information flow diagram including data operations within a content suggestion engine, according to an example described herein.

FIG. 2 illustrates an information flow diagram of an example of data operations 202 of the suggestion engine 102. Data 208A and 208B, illustrated as various inputs, can be provided in a structured format. Structured data, in one example, is unstructured data that has undergone a process of formalization, structuring, categorization, and tagging in the information system. The data operations 202 serve to map data 208A to a personality type 210 or characteristic of the client 106, and an ecosystem of conditions 212 is evaluated to produce appropriate data 208B that addresses one or more environmental goals 204.

Data input for operations 202 of the suggestion engine 102 may originate from a variety of data sets and data types, but some data types and data inputs may not motivate a human subject to attain a particular goal at a particular time. Data 208A can be provided from client personal data, such as location, psychological state, lifestyle, occupation, relationship status, or coaching style, among others, collected or determined for the client 106. A client's personality type 210, such as caregiver, colleague, competitor, authoritarian, optimist, skeptic, fatalist, activist, driver, analytical, amiable, expressive, or combinations thereof, can be inferred or otherwise determined from the data 208A (and changed or adapted as necessary using contextual information 218 or data 208B).

An ecosystem of conditions 212, including barriers 214 to and incentives 216 for achieving the one or more environmental goals 204 can be determined. The ecosystem of conditions 212 generally reflects information items that the information system is aware of, and relevant factors necessary to achieve success. This may include data such as the time of day, client location, medical records of the client 106, and like information or conditions that may affect the client 106.

Barriers 214 considered with the ecosystem of conditions 212 can include the client 106 having a physical ailment, such as a bad knee or asthma, not having a phone, not having supporters, does not like working out, inability to afford the services, having a busy schedule, and medical conditions (such as allergies or taking medications), among others. Incentives 216 considered within the ecosystem of conditions 212 can include things that the client 106 likes (e.g., brand name shoes or specific music), peer pressure, a good feeling gained from performing some activity (e.g., working out), a discount on goods or services provided, or an upcoming event (e.g., a half marathon). The data 208A, 208B and the ecosystem of conditions 212 can be determined through obtaining answers to questions, such as through answers to episodic questions posed to the client 106 (the episodic questions occurring at determined times, places, or contexts). The ecosystem of conditions 212 further may provide contextual information 218 to provide additional data to help interpret or understand the barriers 214, incentives 216, or the data 208A, 208B.

The data 208B can be directly or indirectly related to the one or more environmental goals 204. The data 208B can include a reward for achieving the goal(s) 204 (e.g., kudos), a type of diet to be followed, a reason for wanting to achieve the goal, or a date by which to achieve the goal, among others. The environmental goal(s) 204 may include physical activity goals, such as to lose a certain amount of weight; change a habit, such as to quit smoking, quit biting fingernails, or workout a specific number of times during a period of time; or to achieve a physical challenge such as running a marathon or climbing a mountain, among others.

The one or more environmental goals 204 are not necessarily limited to a central, ultimate goal (such as losing weight, or stopping smoking), but can include a number of subordinate or associated goals (such as developing healthy habits, a positive self-image, or confidence or enjoyment of the goal-reaching process) that help achieve the ultimate goal in a positive fashion. Thus, the environmental goals 204 may be broader than a single goal and can include a number of additive, complimentary, or interrelated actions and results that produce beneficial outcomes and experiences for the human user.

Humans have preferred modes of conversation and interaction. A personality style to invoke these preferred modes can be inferred or determined from answers to questions in questionnaires. The information system 100 can facilitate client 106 completing several questionnaires that show these preferences. The personality styles can indicate a client's receptivity (e.g., the preference for a certain tone of message); engagement (e.g., a bias towards immediate action versus thoughtful consideration when presented with a challenge to change); or social style (e.g., an intersection of assertiveness and responsiveness). The suggested action content delivered from the information system and the content suggestion engine 102 can be designed to fulfill all these preferences.

Figures 3A, 3B:
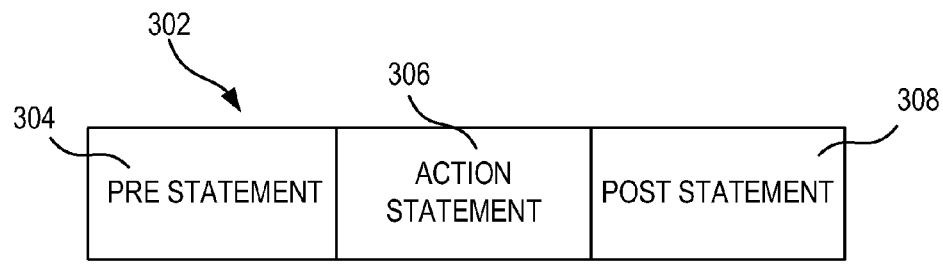
FIG. 3A illustrates a data format diagram including a format for action data consumed by a content suggestion engine, according to an example described herein.
FIG. 3B illustrates a data format diagram including a format for tagging of data consumed by a content suggestion engine, according to an example described herein.

FIG. 3A illustrates a data format diagram including an example of a format for a suggested action message 302 that can be sent to the supporter network 104 or the client 106. A suggested action type of content can be provided from the suggested action message 302, which is sent to the client 106. The suggested action message 302 may include an action statement 306, and a pre statement 304 or a post statement 308 (as further detailed below with reference to FIG. 3). An action statement 306 can include the part of the suggested action message 302 that provides the "do this" statement; a pre statement 304 and post statement 308 can include the part of the suggested action message 302 that personalizes the tone of the "do this" statement (these statements precede and follow the action statement, respectively). Examples of action statements 306 are shown in FIG. 3B.

The pre statement 304 or post statement 308 can be tailored to fit the personality type 210 of the client 106. For example, if the client 106 is determined to have a competitor personality type 210, the pre statement 304 can be "Your teammates and supporters are watching"; "We need you"; or "It's coach [insert name] here . . . "; among others.

The action statement 306 can convey the suggested action to the client 106, such as "you are going to the park today"; "you are going for a run today"; "you are going to eat a salad today"; among others. The post statement 308 can be an encouraging or motivating statement that is tailored to the personality type 210 of the client 106.

In the example of the client 106 with the competitor personality type 210, the post statement can be a statement such as: "You cannot win if you do not try"; "You will have the best day of anyone this week"; or "On your marks, get set, go"; among others.

Further, the structure of content can include an action statement (e.g., a recipe), pre statement, or post statement, customized to: specific psychological typing; motivational content; prompts; greetings; rewards; or messages to supporters. Suggested actions can "personalized" to a client's personality type 210. An action statement 306 can be preceded with a pre statement 304 (e.g., a greeting), and followed with a post statement 308 (e.g., appropriate reminders, prompts, or motivations). Completion of, or non-completion of, a suggested action message 302 can be followed by either a reward (e.g., kudos) or motivation intended to keep the client 106 trying again, respectively.

Content Delivery Programs for Suggested Content

A playlist is a set of suggested actions (each action containing suggested content) that can be presented to the client 106 as a single "set of suggested actions." This can make the choosing of actions less frequent, and provide a short term context for the client 106. The client may desire repetition, variety, concentration on a particular area, or to be generally healthy. Playlists can be designed to link suggested actions together to create a coordinated effort that can consider client desires.

The playlist(s) can be chosen as a specific item by the client 106. The playlist may include suggested actions during a period of time, such as a day, week, ten days, months, quarter, year, and so forth. The client 106 may wish to choose a (somewhat) coordinated effort that is longer than a single action (e.g., making sure they eat a healthy breakfast for one week). The playlist feature can allow the client 106 to choose this as a single item. Each suggested action message 302 in the playlist can be set for specific times as designated in the playlist (e.g., every x period).

A program can be: 1) a designation of a specific type of suggested action message 302 defined in keywords (e.g., Mayo Clinic diet, weight watchers diet, etc.), where the suggestion engine 102 preferentially chooses actions or playlists to present to the client 106 as a function of the keywords; or 2) a set of playlists presented in a series, such as a series that has a defined objective (for example, eat a good breakfast for four (4) weeks, which can include a suggested action message(s) 302 for both purchasing the materials for a good breakfast, such as oatmeal, as well as allowing enough time to eat it before starting the day's other activities).

For programs of type 1, the client 106 can be offered the option of choosing a program to follow. For programs of type 2, users, such as employees or professional supporters, can create programs by selecting a series of playlists, and then giving a definition, keywords, or additional tags to be included by the program. The program can include a "creator" designation for the user who created the program and the "creator" can title the program. Choosing a program can give the client 106 context for why they are performing the specific eating/movement/self-view action(s).

A goal 204 set by the client 106 can be a powerful motivation. The goal 204 can be used to determine what percentage of the suggested action messages will be, for example, in each of the eating/movement/self view areas. The goal 204 can be used to motivate the client 106 by reminding them of the specific goal 204 they have chosen.

The suggestion engine 102 can deliver appropriate suggested action content to the supporter network 104 or client 106 as a function of a set of rules. These rules can include how the content will be delivered to the client 106 or supporter network 104. The suggestion engine 102 can determine one or more suggested action message(s) 302 or playlists based on the client's psychological, lifestyle, preference and restriction assessment, or the client goal(s) 204. The suggested action message 302 can be sent to the supporter for forwarding on to the client 106 or directly to the client 106 depending on rules or preferences.

The content can follow a general flow. The client 106 can be presented with a number of suggested action messages (or playlists), from which they can choose one or more. The suggested action message 302 can be presented as just the action statement 306 with no personalization. A timer of a specified period, such as twenty-four hours, can start at or near the time the suggested action is chosen. The suggested action can have a designated time of day associated with it, such as morning if the action is breakfast, for when a reminder should be sent—the client 106 can designate times that they regularly do things like breakfast, lunch, or dinner, when they exercise, and when they struggle with being hungry. When the client 106 has not set preferred times when choosing a suggested action message 302, the system can ask the client 106 when they typically do that type of action.

One or more reminders can be sent to the client 106. The reminder can include personalization, and the reminder can be provided at the beginning of the next day, or at or near a designated time. A motivation or prompt can be sent to the client 106 at times before or after the reminder. A prompt can be sent to the client 106 after the specified period of time has lapsed. This prompt can ask the client 106 if they have completed the suggested action. If the client 106 has completed the suggested action, they can be rewarded with reward points (also referred to herein as "kudos") or given a congratulatory motivation. If the client 106 has not completed the suggested action, they can be given a conciliatory motivation, such as "you will get it next time!!". The client 106 can be asked if: 1) they would like to try again; or 2) move on to the next suggested action, or something similar. If the response is to try again, the previous action can be presented at the appropriate time with appropriate motivations and prompts; and if the response is to move on, the system can log the incomplete suggested action as not completed and send the client 106 to the next task. If the client 106 has chosen a playlist of suggested action messages, the steps above can be substantially followed, such as without being asked if they would like to try again. If the client 106 does not perform a suggested action they can be presented with a conciliatory motivation, and then reminded of the next task in the play list. When the client 106 is sent a suggested action message 302 from a playlist, the playlist name, or the order of the suggested action message 302, can be included in the information available to the client 106.

An action statement 306 defines the action being sent to the client 106, such as "Take a walk in a park"; "Try this recipe"; or "Write the day's best moments in your journal before you go to bed"; among others. A pre statement 304 and a post statement 308 can provide a short statement that personalizes the suggested action 304 for a specific personality type 210. The personalization can be accomplished by having a person use a database of personalization examples to create the entire suggested action message 302, and filtering the created suggested actions messages, such as by using the content suggestion engine 102, to help insure the language used is appropriate. Tagging of the suggested action can be accomplished by having a unique tag for the action statement 306, one that defines the relevant personality type 210, or both.

After the client 106 has chosen a suggested action, the system can provide an appropriate motivation, prompt, reminder, or reward statement. The number of motivations, reminders, and prompts can be defined in a suggestion engine 102 database, and can be based on the client's psychological assessment. A psychological assessment can include determining a receptivity of the client 106 to a motivational or encouraging statement, such as whether the client 106 is a caregiver, colleague, competitor, or authoritarian; a client's engagement in achieving their goal 204, such as whether the client 106 is an optimist, fatalist, activist, or skeptic; a client's social style, such as whether the client 106 is a driver, amiable, analytical, or expressive; or a combination thereof. For example, a message for a caregiver can take the form of admonition, communicate to the client 106 that the substance of the message is good for them, or be supportive yet directive. Such persons can tend to assume a hierarchical relationship in which they have some form or power over another, yet tend to be more challenging than nurturing in their interactions. A message for an optimist can include encouragement to act, support or pressure from their social network, increasingly persistent reminders to act, or a combination thereof. Such persons may tend to think about the suggested action, search for ways to ensure success, overthink or overplan, or have a high level of excitement that can diminish without action. A message for an analytical person can include statistics or data that provide support for why the action should be accomplished, or it can be more task-oriented rather than person oriented. Such persons can be perfectionists, critical of themselves, systematic or well-organized, prudent, or a combination thereof.

Data Formats and Data Tagging

FIG. 3B illustrates a data format diagram including an example of a format 310 for tagging of data consumed by a content suggestion engine 102. As illustrated, the format 310 defines a series of tags (difficulty 314, duration 316, behavior change 318, and restrictions 320) for a set of action statements 306. For example, the action statement 306 "Walk in the Park" may be tagged with a tag for difficulty 314 of "Low"; for duration 316 of "15 Minutes"; for behavior change 318 of "Social"; and for restrictions 320 of "Mobility." FIG. 3B further illustrates the application of these tags for other action statements 306 such as "Eat Oatmeal Breakfast," "30 Minute Rollerblade," and "Eat Whole Grain Cereal."

A pre statement 304, post statement 308, or action statement 306 can be tagged. The action statement 306 can be created by writing, finding, or otherwise defining relevant actions. For example, to pursue actions relevant to weight loss, actions relevant to exercise may include walking, jogging, running, soccer, hockey, tennis, gardening, yard work, swimming, rollerblading, basketball, football, Frisbee, weight lifting, stairs, jump roping, kickboxing, zumba, biking, yoga, pilates, dancing, bowling, volleyball, racquetball, rowing, softball, baseball, skating, skiing, tubing, eating, snowboarding, water boarding, boxing, taking pictures, writing, and the like. Action statement tags relevant to weight loss may be directed to tags such as eating, movement, self-view, behavior change category, personality type, difficulty, time duration, timeliness, lifestyle, restrictions or limitations, or combinations thereof. If an action or statement could be more than one of these areas, both areas can be tagged.

The action statement 306 can be personalized, such as by choosing a pre statement 304 or a post statement 308, such as from pre-drafted, or templates of, pre statements 304 or post statements 308. The pre statement 304 or post statement 308 can be combined with the action statement 306. The resulting suggested action message 302 can be edited into engaging, appropriate, coherent language, such as by editing the pre statement 304 or post statement 308 to include reference to the action statement 306 by making it unique to the action statement 306; or by adding an explanation of the action, such as by adding a picture or video to help describe the action statement 306. The explanation or a link thereto can be stored along with the suggested action message 302 in a suggested action database 904 (see FIG. 9).

In some examples, a behavior change tag can include an individual's intrinsic/extrinsic motivation, such as for suggested actions intended to help the client 106 engage in the activity of the suggested action; individual aptitude such as for a suggested action intended to help improve knowledge, skills, and strengths to do the activity; group factors, such as for suggested actions intended to have other people (e.g., a supporter from the supporter network 104) encourage the client 106 to perform the suggested action or refrain from a deleterious behavior; group power for causing behavior change, such as for suggested actions intended to provide help, information, or other resources, and at a particular time; environmental factors, such as for suggested actions intended to provide a reward, promotion, perk, or cost, such as to encourage the suggested action or discourage deleterious action; environmental power for causing behavior change, such as for a suggested action intended to help the client 106 stay on course; or combinations thereof. A balanced set of actions from many of the behavior change areas can improve the probability of the client 106 meeting their goal(s) 204. The system can promote this balanced set of actions by tracking the behavior change areas chosen, and providing a suggested action message 302 including a tag from those behavior change areas that have been performed less often by the client 106 (e.g., are not as successful).

In some examples, a psychological assessment tag can be associated with a pre statement 304, action statement 306, or post statement 308, such as to match a personality type 210 to the respective statement.

In some examples, a difficulty tag 314 can be associated with a pre statement 304, action statement 306, or post statement 308, such as to indicate how hard the task is to complete, or to associate a pre statement 304 or post statement 308 to an action statement 306 of corresponding difficulty. The difficulty tag 314 can indicate whether the suggested action is easy to execute (e.g., beginner or low difficulty) or that the suggested action does not take a lot of resources (e.g., time, money, or expertise, to execute); involves some difficulty (e.g., medium difficulty) in executing (e.g., capability of the human) or that the action requires some resources to execute; or whether the suggested action is difficult (e.g., high difficulty) to execute (e.g., expert input) or requires a significant amount of resources.

A lifestyle tag can include typical times for actions to be presented, such as suggesting breakfast in the morning, or if the client 106 indicates he or she tends to wake up at a certain time then suggesting breakfast shortly after they wake up.

A quality check of at least part of the suggested action message 302 (e.g., combination of pre statement 304, action statement 306, and post statement 308) can be performed before the suggested action message 302 is delivered to the client 106. The pre statement 304 can be a short message that references an action statement 306 and provides the action statement 306 with a psychological match. The pre statement 304 and post statement 308 can be matched, such as to be used together with an action statement 306. The pre statement 304, post statement 308, or action statement 306 can be edited for length or sentence structure, such as to be coherent or include less than or equal to a certain number of characters, such as 140 characters (for example, for delivery by short message service (SMS), Twitter, or other messaging services). The edited statements can be recorded in a database (e.g., the suggested action database 904 illustrated in FIG. 9) as templates for use in future statements.

Other possible types of tags can include motivational, prompt, greeting, reward, or combinations thereof. A message (e.g., a suggested action message 302) can be tagged as a message to a supporter, such as for suggested actions that are intended to promote a supporter to engage the client 106.

Like an action statement 306 or suggested action message 302, a playlist can include a name, keyword, description, or timing constraints. Reminders can be created to let the client 106 know that the suggested action 302 in a playlist will expire in a specified period of time. The system can include rules, such as in a rules database 904 (see FIG. 9), for how many playlists can be running at a time, such as no more than three playlists can be running at any given time for the same client 106. The playlist can be presented to the client 106 in a manner similar to how a suggested action is presented.

A client 106 can choose a program with specific keywords or descriptions, such as a keyword or description that is provided with a suggested action or playlist. This can help the system match a client 106 already using other programs with a suggested action appropriate to that program or client 106. This can also help professional supporters set up a program for the client 106 to follow. For example, if the client 106 chooses a program for following a Mayo Clinic-approved diet, the suggestion engine 102 can provide a suggested action 302 or playlists to the client 106 with "Mayo" in the associated keyword or description. The program can have a name, keywords, or description (similar to the action statement 302). The description can include the timing of the playlist. Each action in a playlist can expire in a specified amount of time. Reminders can be created to let the client 106 know that the suggested action 302 in a program will expire. Rules for how many programs can be running at the same time can be defined, such as a maximum of three programs that can be run for a client 106. Delivery of the program to the client 106 can be similar to delivery of a suggested action. Programs can be approved by a system user, such as a system administrator, prior to allowing client access to the program.

As a more detailed example of tagging, suggested content may be tagged with one or more tags to indicate various attributes of content and content items. For example, a set of textual characters, a code, or another identifier may be associated with particular attributes for application to content items. A single tag may be associated with a plurality of content items, establishing a one-to-many relationship.

As an example of the application of a tag that indicates "Timeliness," and designates that a tag should be sent during a specific time during the day, the following tags may be applied:

TABLE 1

| "Timeliness" Tags | |
|---|---|
| Timeframe | Tag |
| First thing in the morning (breakfast, getting up, etc.) | MOR |
| Noon time (lunchtime, etc.) | NOO |
| Early afternoon (2-4 PM) | EAF |
| Evening (dinner time, etc.) | EVE |
| Right before bedtime | RBB |

As an example of the application of a tag that indicates "Physical Restrictions," the following indicates restrictions to designate activity in which the human user should not be engaging, such as what food the human user should not eat. For example, if the client 106 cannot or should not be engaging in activity per a doctor's order, the following tags may be applied. Restrictions may be applied on a temporary or permanent basis.

TABLE 2

| "Physical Restrictions" Tags | |
|---|---|
| Type of Restriction | Tag |
| Weight-bearing on hips, knees, or ankles | WBLE |
| Weight-bearing on arms, elbows, wrists, fingers | WBUE |
| Milk allergy | MA |
| Citrus allergy | CA |
| Egg allergy | EA |
| Peanut allergy | PA |
| Tree nut allergy | TA |
| Shellfish allergy | SA |
| Wheat allergy | WA |
| Soy allergy | SYA |
| Gluten Allergy | GA |
| Vegetarian | V |
| Kosher | K |
| Halaal | H |

As another example, a tag may be applied to multiple sets of data points and data values. For example, in categories of poor self-image detected for a client, multiple detected problems may stem from a common tag:

TABLE 3

| Tags Applied to Multiple Content Items | | |
|---|---|---|
| Low self esteem | SVSE | Poor body image - not toned enough<br>Poor body image - too much fat |

TABLE 3-continued

| Tags Applied to Multiple Content Items | | |
|---|---|---|
| Poor self talk | SVST | Negative self talk that focuses on flaws, mistakes<br>Negative talk that focuses on not being able to do something or achieve a goal |
| Lack of accurate visual perception of self | SVP | Seeing they are more overweight than they actually are |
| Fear | SVF | Fear of failing<br>Fear of succeeding<br>Fear of looking foolish or silly |
| Unsupportive conversations (family, social) | SVUC | Conversations with family and friends around not being able to lose weight<br>Conversations with family and friends around the benefits about the status quo |
| Lack of integrity | SVI | Lack of follow through<br>Not truly committing to an action |
| Lack of action | SVA | Lazy<br>Competing priorities |

Another example of tagging that may be applied as a psychological attribute is a "behavior change" tag. Behavior change tags may be applied to identify suggestion action items that improve an individual's motivation and aptitude, group factors and power, and environmental factors and power to help change their behavior. In one example, six behavior change areas corresponding to personality types and psychological profiles are defined and applied as tags to various content:

| | |
|---|---|
| Individual's intrinsic/extrinsic motivation | Find ways to have the individual desire to engage in the activity |
| Individual aptitude | Have the individual improve the knowledge, skills, and strengths to do the right thing even when it's hardest |
| Group factors to behavior change | Have other people (supporters) encouraging the right behavior and discouraging the wrong behavior |
| Group power to cause behavior change | Have others provide the help, information, and resource at particular times |
| Environmental factors causing behavior change | Make rewards, promotions, perks, or costs encouraging the right behaviors and discouraging the wrong behaviors |
| Environmental power to cause behavior change | Make sure there are enough cues to stay on course. Have the environment (tools, facilities, information, reports, proximity to others, policies) enable the right behaviors and discourage the wrong behaviors |

Application of each of these areas as tags to suggested action content enables customization in a context-sensitive fashion. For example, the use of certain types of suggested actions tagged with an "individual aptitude" tag may be appropriate to a human subject at one point in time; whereas suggested actions tagged with a "group factors" or "environmental factors" tag may be more appropriate to the human subject at other times. A psychological profile of the client 106 (which may be adapted over time) may also indicate the types and amounts of usage of the various categories.

The theory behind this behavior change model states that these areas improve the probability of a human subject making the desired behavior change. These tags may accordingly be used on action statements provided by the content suggestion engine 102. The content suggestion engine 102 will be able to track the clients' use of the action statements in each of the areas and preferentially suggest actions that have many areas included.

These behavior change tag types corresponding to personality profiles may also be used to directly affect the type, format, and result of pre statements 304, action statements 306, and post statements 308. In one example, the communication style may be provided from a variety of customized profiles, such as Caregiver, Colleague, Competitor, Authoritarian, and the like, to tailor the content of a suggestion action message 302.

TABLE 4

Suggested Action Messages by Communication Style

| Pre statements | Action statement | Post statement |
|---|---|---|
| *Communication Style: Caregiver* | | |
| This is you being really healthy: | You are going to the park today to take some pictures - | This is what healthy looks like. |
| It's time for your "medicine." | | You'll feel great after. |
| Your healthy actions are ready: | | You'll have a great time. |
| Ready (or not), | | You can do this. |
| This is your caregiver (name) coming to you live . . . | | We're sure it's going to be great. |
| *Communication Style: Colleague* | | |
| Time for you to get going, | You are going to the park today to take some pictures - | We're all in this together. |
| Hey, it's time for | | Every time you do this, it's one more step to being healthy. |
| Woohoo, it's time for: | | We're rooting for you. |
| *Communication Style: Competitor* | | |
| Your teammates and supporters are watching . . . | You are going to the park today to take some pictures - | You can't win if you don't try. |
| We need you. | | You'll have the best day of anyone this week. |
| Are going to let all those youngsters beat you? | | You'll be the best looking there. |
| Wow, are you going to look good today . . . | | On your marks, get set, go. |
| You need some kudos, Mary. | | |
| *Communication Style: Authoritarian* | | |
| Off your duff lady. | You are going to the park today to take some pictures | We'll check in after you get back. |
| It is time for some action . . . | | Remember, do what you say. |
| Get ready for your activity, Mary. | | You can let me know how it went later. |
| You signed up for this. Let's get moving. | | Go, go, go! |
| Come on, Mary. Time to get going | | You can do it, so do it. |

Suggestion Engine Operation

The suggestion engine 102 operates to determine what type of suggestion content (e.g., pre statement, action statement, post statement, or combinations thereof) can be chosen for presentation through the supporter network 104 or to the client 106. The suggestion engine 102 can determine what content is appropriate based on questions that the client 106 answers or a set of rules that can be applied to both restrict and narrow content, such as by weighting and filtering the suggested actions.

Figure 4:
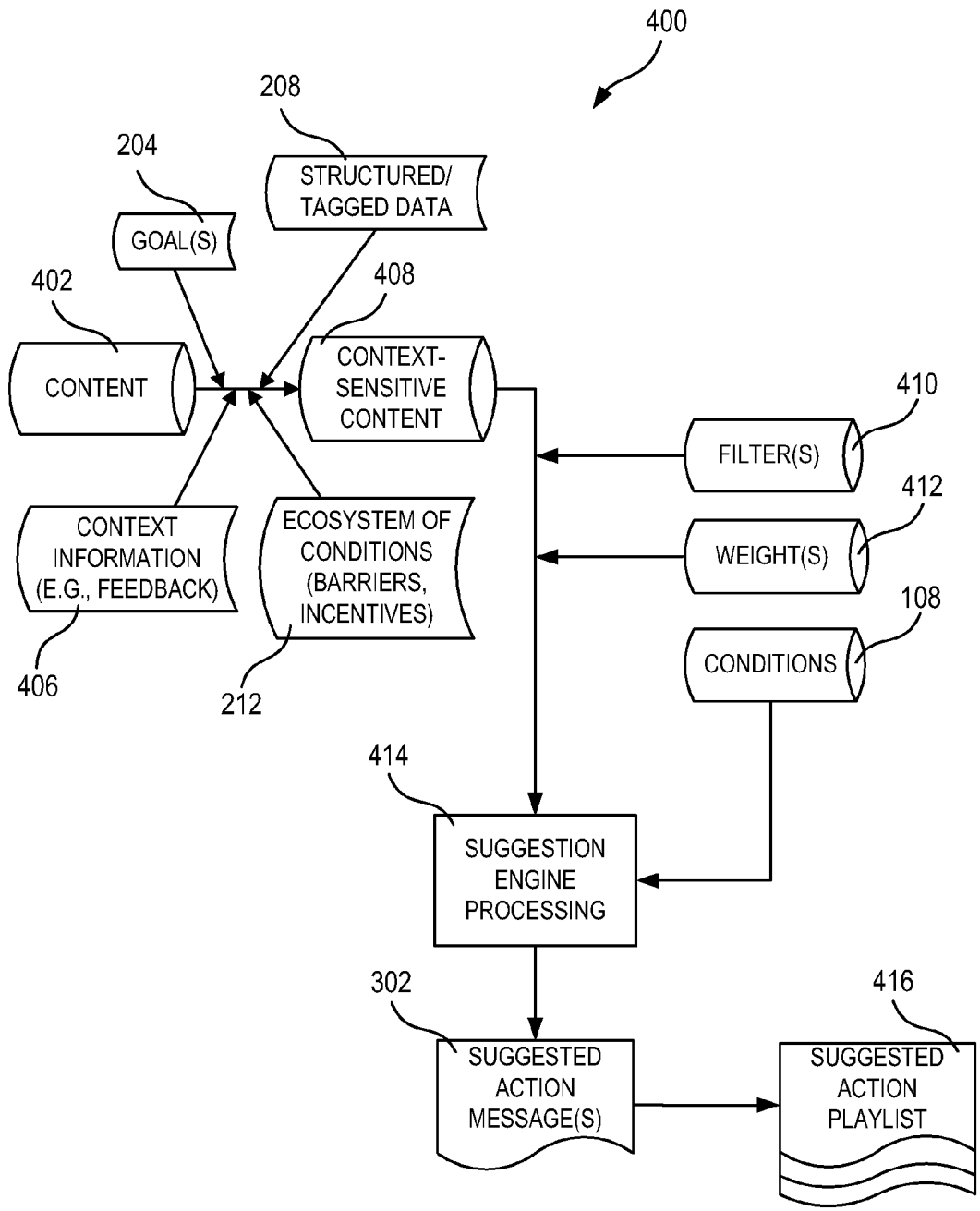
FIG. 4 illustrates a data source diagram of data sources for a content suggestion engine, according to an example described herein.

FIG. 4 illustrates a diagram for a data processing technique 400 involving example data sources and data outputs for a content suggestion engine 102. The data sources can include content 402, goals 204, structured and tagged data 208, data from the ecosystem of conditions 212 (e.g., barriers, incentives), or context information 406 (e.g., feedback), among others.

Content 402 can include data gathered from data-mining databases, information or suggested actions provided by a user such as the client 106 or the supporter network 104, or other content provided from sources internal or external to the information system. Context information 406 can include feedback from the client 106 or the supporter network 104. For example, the applicable feedback can include whether the client 106 liked or disliked a suggested action, the client's perceived effectiveness of the suggested action, whether or not the suggested action was too difficult, too easy, or a good fit, how the client 106 felt after completing the suggested action, and the like.

Context information 406 may include a variety of information relevant to the status of the goal 204, the client 106, or the client's ability to reach the goal 204 or activities (e.g., completion status of a suggested action) relevant to the goal 204. This may be as simple as feedback from episodic questions delivered to the client 106 to determine the client's current mode, psychological state, or physical state. More complex short-term and long-term feedback such as an analysis of client location, client activity, or client longer-term life plans may also be considered. The context information 406 may be derived from real-time historical information.

The context-sensitive content 408 can be filtered with one or more filters 410, weighted with one or more weights 412, and provided for processing 414 by the suggestion engine 102. The suggestion engine processing 414 can include formatting for the data so as to be appropriate for the client 106 or determining which suggested action message(s) 302, suggested action playlist 416, or program to present to the client 106 or supporter network 104.

Suggested action content and accompanying suggestion action messages 302 can be determined from suggestion-based context information 406 and data conditions 108 (e.g., psychological profile, medical conditions, lifestyle, demographics, and goals) of the client 106. Examples of context information 406 may include detailed information for the client's purpose, such as what the client 106 wants to achieve as a goal 204 (e.g., look better, feel better, be more healthy, lose weight, run a marathon, etc.), problems keeping the client 106 from achieving the goal 204 (e.g., ignorance, bad habit, unsupportive environment, is too busy, does not want to perform actions, is disinterested, has emotional issues, etc.), likes and dislikes of the client 106 (e.g., the client 106 will not do some actions), information gained from or inferred from answers to questionnaires, behaviors that make more of a difference than others (e.g., weigh yourself, eat breakfast, exercise, etc.), or combinations thereof, among others. The system can use structured and tagged data 208 and other information gathered about the specific client 106 to help the system narrow down the suggested action message(s) 302 delivered to that client.

Assessments or questionnaires can be used to gather context information 406 about a client 106. The context information 406 gained from questionnaires can be used in various ways. Examples of questionnaires include psychological, such as to determine the personality traits of the client 106; personal, such as to determine demographics of the client 106; likes/dislikes/exclusions, such as to give weight to either include or exclude specific actions or playlists based on suggested action keywords or descriptions; lifestyle, such as to determine the client's problems, and give weight to a playlist, program, or suggested action defined for specific solutions; or actionable goal(s), such as to provide weight for movement, eating, or self view suggested actions, to be used for motivation.

A variety of episodic questions, determined feedback, and other real-time or timely values from context information 406 may be used in the suggestion engine 102 to produce the context-sensitive content 408 with an increased relevance to the goal 204 and to the client 106. To narrow the list of possible suggested actions, restrictions, dislikes, or previously rejected suggested action messages 302 or content can be filtered out by the suggestion engine 102, such as by using filter(s) 410. A priority list also can be used to alter the weight(s) 412 of a filtered suggested action, or playlist 416 of suggested action messages 302 (for a particular client 106 or set of clients) using appropriate context information 406, data conditions 108 of the client 106, and other appropriate contextual data.

Figure 5:
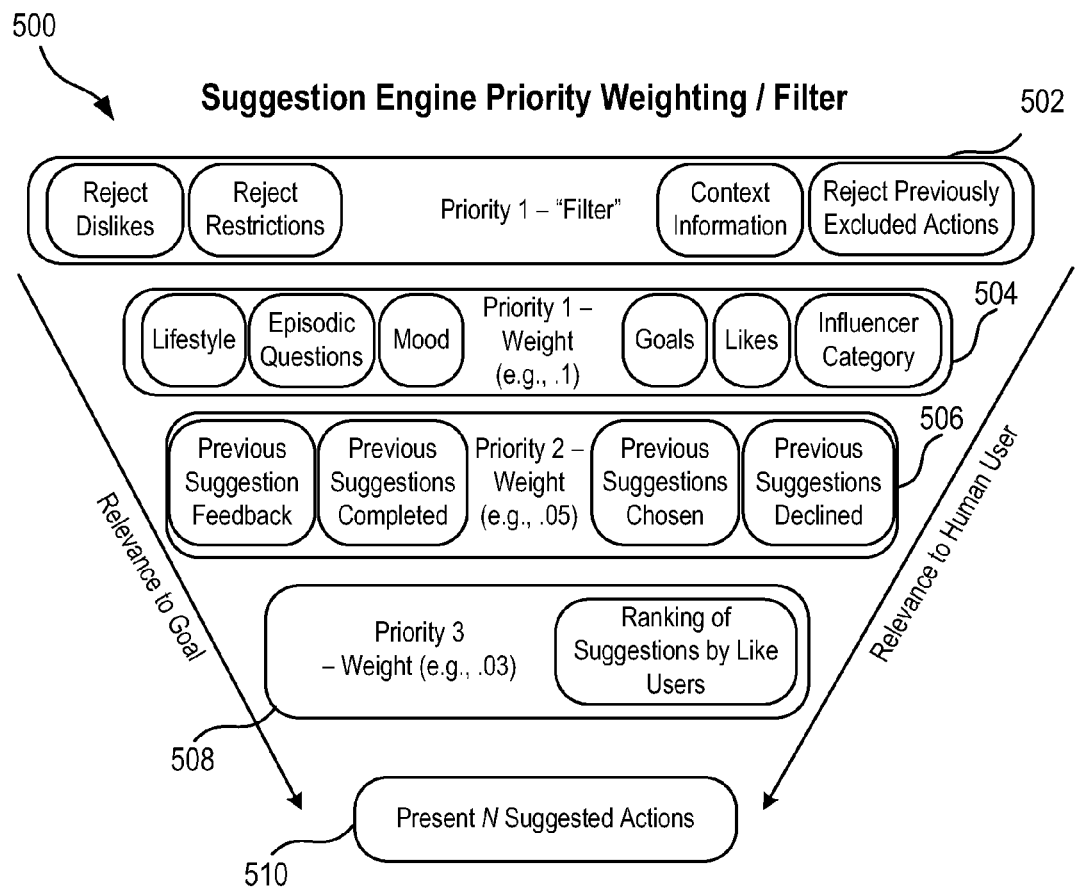
FIG. 5 illustrates a block diagram for filtering and weighting operations applied within a content suggestion engine, according to an example described herein.

FIG. 5 is a block diagram of an example of a technique of filtering and weighting suggested action content 500, such as a technique that can be implemented by the content suggestion engine 102. As illustrated, the product of the filtering and weighting suggested action content is the selection or presentation of N number of suggested actions 510, where N is an integer greater than zero. In one example, the suggestion engine 102 can be used to create three (3) suggested actions at a time for presentation to the client 106. Three suggested actions can allow the client 106 to filter and select a definite preference among choices, without presenting too large of a number of choices. Other suitable numbers of suggested actions (or a single selected suggested action) may be used in other examples.

At operation 502, suggested action content can be removed (e.g., filtered using filter 410) from a set of possible content to send to the client 106. Removed content can include content including activities or activity subjects that the client 106 dislikes, actions that a client 106 cannot accomplish because of a barrier 214 (e.g., physical restrictions), or previous suggested actions that were rejected by the client 106 (e.g., a suggested action that was rejected by the client 106 where the client 106 indicated that they did not want to see that suggested action again). The filter may also factor in various types of real-time feedback, such as context information 406 produced from monitoring, episodic questions, profiling, machine learning, and other timely feedback related to the client 106.

At operation 504, the suggested action content can be weighted based on high importance priorities, such as the suggested action content being relevant to the client's 106 lifestyle, problem(s), goal(s), likes, answers to episodic questions, current or historical mood, or psychological profile tags and categorizations such as a behavior change tag 318. Other information related to the type and result of incentives 216 and barriers 214 may also factor into the high importance weighting.

At operation 506, the suggested action content can be weighted based on medium (e.g., average) importance, such as the client 106 previously completing a related suggested action, choosing the suggested action, declining the suggested action, or providing feedback related to the suggested action.

At operation 508, the suggested action content can be weighted with a lower priority, such as when the suggested action has been liked or completed by a client 106 with a similar profile as the client 106 to whom the suggested action is being provided. Low importance weighting may also factor input from supporters in the supporter network 104 and other users.

At operation 510, a number N of suggested actions 302 including the suggested action content can be presented to the client 106, for immediate presentation or for presentation as part of a suggested action playlist 416. Associated suggested action messages can be presented as a function of the weighting. As discussed above, the number, type, and format of the suggested action messages selected or presented may depend on the delivery medium, user preferences, and a variety of other factors.

Weights applied by the suggestion engine 102 may vary in application. A client 106 can have weights 412 that are added or subtracted to a particular suggested action content or suggested action message 302, based on data from a questionnaire. The weights 412 can change the effective rating of a suggested action, such as to determine which suggested actions 302 can be sent to a supporter in the supporter network 104 or to the client 106. For example, if the weight(s) 412 of a suggested action 302 range from 0 to 1.0, then the following weight additions or subtractions can be used. The suggestions can begin with a weight 412 of 0.5. The weight 412 can increase by 0.1 if a problem is determined from a lifestyle questionnaire, and a suggestion, playlist, or program includes that problem as a keyword or in the corresponding description. In some instances there can be more than one problem, and when that occurs, such as when all other factors are equal, a heuristic can be followed to determine which problem will be improved first, such as a heuristic that indicates to help an eating problem first, a movement problem second, and a self-view problem third.

Heuristics can be provided for sub-problems within each problem set. For example, eating problems can be broken into eight subsets, in order of importance in this example: 1) ignorance; 2) lack of support, 3) time restriction; 4) portion control; 5) inconsistency; 6) mindlessness; 7) emotions; 8) perceived reward. Similarly, the movement and self-view problems can be broken up into sub-problems and prioritized. A client 106 can choose the priorities (e.g., importance of these problems). The heuristic of the problems or sub-problems can alter the weight of suggested actions, such as to increase suggested actions in categories linearly from 0 to 0.1. For example, if eating is very important and movement and self view are less, then all eating suggested actions can have an increased weight by 0.1; or if eating is in the middle between very important and less important, with movement and self view less important, than eating suggested actions can have an increased weight of 0.05.

The client 106 can be asked by the system to choose activities that they like, which can also provide weighted effects. A suggested action message 302, playlist, or program can be tagged to be matched to a client 106 with that tag as a like. Certain likes, such as "eating" likes in a weight loss scenario, can be excluded from these matches. Suggested actions with matching likes can have an increased weight, such as an increased weight of up to 0.1.

A suggested action taken, completed, or ignored in all six behavior change tagging categories (as discussed above) can affect the probability of creating a behavior change. The suggested action(s), playlist(s), or program(s) can be tagged for the behavior change area. The client 106 can have a "behavior change scorecard" showing how many times a suggested action, playlist, or program with a behavior change tag in a behavior change area has been completed.

The weighting can be increased for the suggested action in behavior change areas less completed, such as by up to 0.1.

A previous suggested action not chosen can have a weight of 0.0 or some other nominal value. Such suggested actions can be suggested again in a specified period of time (e.g., after a withhold time), such as suggesting the not-chosen suggested action in three days. If a suggested action is not chosen multiple times in a row, then the not chosen suggested action can have the withhold time increased, such as not suggesting the not chosen suggested action for one month. A previous suggested action chosen (but not completed) can have an increased weight, such as an increased weight of below 0.03. A previous suggested action chosen and completed can have an increased weight, such as an increased weight of below 0.05. A previous suggested action completed with feedback can have a decreased weight, such as a decreased weight below 0.05, for poor helpfulness with a linear increase of up to 0.05 for a high helpfulness rating.

Some clients can have similar personality traits and can be labeled as similar. The "similar" designation can be a function of personal data and questionnaires filled out. A comparison of problems, goals, age range, body mass index (BMI), children (number or age), or work status, among other things, can be used to determine similarity. The weighting of suggested actions for a client 106 can be an average of the weights determined by a specific number of most similar clients, such as the top fifty most similar clients.

Dynamic Content Delivery and Feedback

The content suggestion engine techniques and operations described herein may also incorporate a variety of machine-learning and artificial intelligence concepts to adapt to context information 406 (such as feedback), and deliver the content to the client 106 using appropriate timings and mechanisms. As the content suggestion engine 102 produces suggested actions and obtains client feedback, the content suggestion engine 102 can start to learn what is successful, and apply greater weight to a particular suggested action with a higher likelihood to succeed, thereby producing a cycle of improvement with a greater likelihood of progress towards goals 204.

Figure 6:
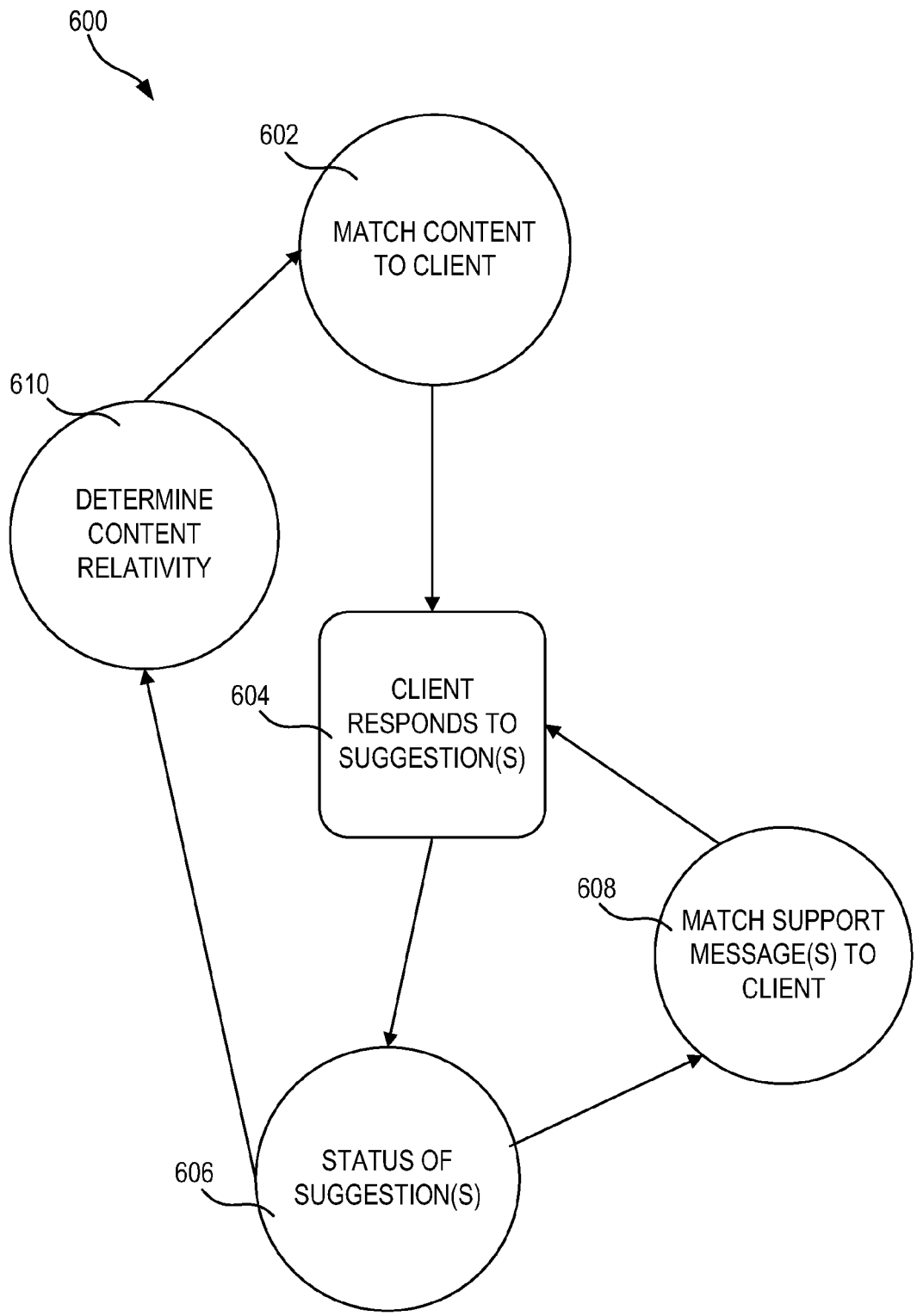
FIG. 6 illustrates an example technique of client interactivity with suggestions from a content suggestion engine, according to an example described herein.

FIG. 6 illustrates an example technique 600 of client interactivity with a suggested action generated from a content suggestion engine 102. At operation 602, content can be matched to a client 106, such as through data processing technique 400, and filtering and weighting technique 500. At operation 604, the client 106 can respond to the suggested action, such as by accepting or rejecting the suggested action message 302. A no-response within a period of time may also serve as a response. At operation 606, the status of the suggested action can be determined, such as determining if the suggested action message 302 was accepted or rejected, or when the suggested action message 302 is accepted and whether the action in the suggested action message 302 is completed or not. At operation 608, a support message can be sent to the client 106, such as sending the client 106 an encouraging or motivating message to try to get the client 106 to complete the action. At operation 610, content relativity can be determined, and such relativity can be recorded for use in a future suggested action.

If questionnaires or psychological profiling indicate that a problem exists in an area (e.g., movement, eating, self view, etc.) that is different from the goal(s) 204 created by the client 106, then the system can ask the client 106 to review the goal(s) 204 or suggest the client 106 add another goal and indicate what that goal is. The system may also encourage the client 106 to achieve the goal 204 by giving reward points (e.g., kudos) or other incentives.

As a new client signs into the system and is given the opportunity to complete questionnaires or to begin a suggested action, he or she can decide to use the system right away without filling out much information about them. These clients can be given a suggested action without much data about the client 106 that the suggestion engine 102 can process. A new client also can choose a program from a group of pre-created programs. These programs can include suggested actions that encourage the client 106 to achieve goal(s) 204 related to movement, eating, or self view, encourage the client to perform suggested actions that help them learn the different features of the system, record how the client 106 uses the system, and suggest that the client 106 complete questionnaires, at intervals or regularly. Getting feedback on a suggested action can help the suggestion engine 102 determine which suggested action to recommend to the client 106 after the program is complete.

When completed, the suggested action can be put back into the suggested action database 910. Any completed suggested actions can be withheld from retrieval from the suggested action database 910 for a specified period of time. Such withholding time can be based on a client preference, such as the client 106 indicating that they prefer variety or sameness in the suggested action messages 302 that are presented to them. For example, if a client 106 indicates that they prefer variety, a completed suggested action can be withheld for a longer period of time than if the client 106 indicates they prefer sameness.

A goal can be said to be accomplished when the client indicates the goal has been accomplished or when the system determines that the goal has been accomplished. For example, the system can ask the client 106 or the client's supporters if the goal has been accomplished.

A client 106 can indicate that the suggested action was not timely. In such situations, the system can ask the client 106 when the suggested action message 302 would be or would have been timely. A timing tag related to a suggested action message 302 can be adjusted accordingly. Timing tags can indicate an amount of time that the client 106 can be given to complete the task, such as 15, 30, 45, 60 minutes, or the like.

The difficulty rating (a tag) of a suggested action can be altered in accordance with client feedback. The weight of a suggested action can be altered as a client's ability to complete a type of suggested action changes. For example, if a client 106 rates a suggested action as too hard, the weight of the suggested action can be decreased, and the weight of suggested actions with lower difficulty can be increased.

Figure 7:
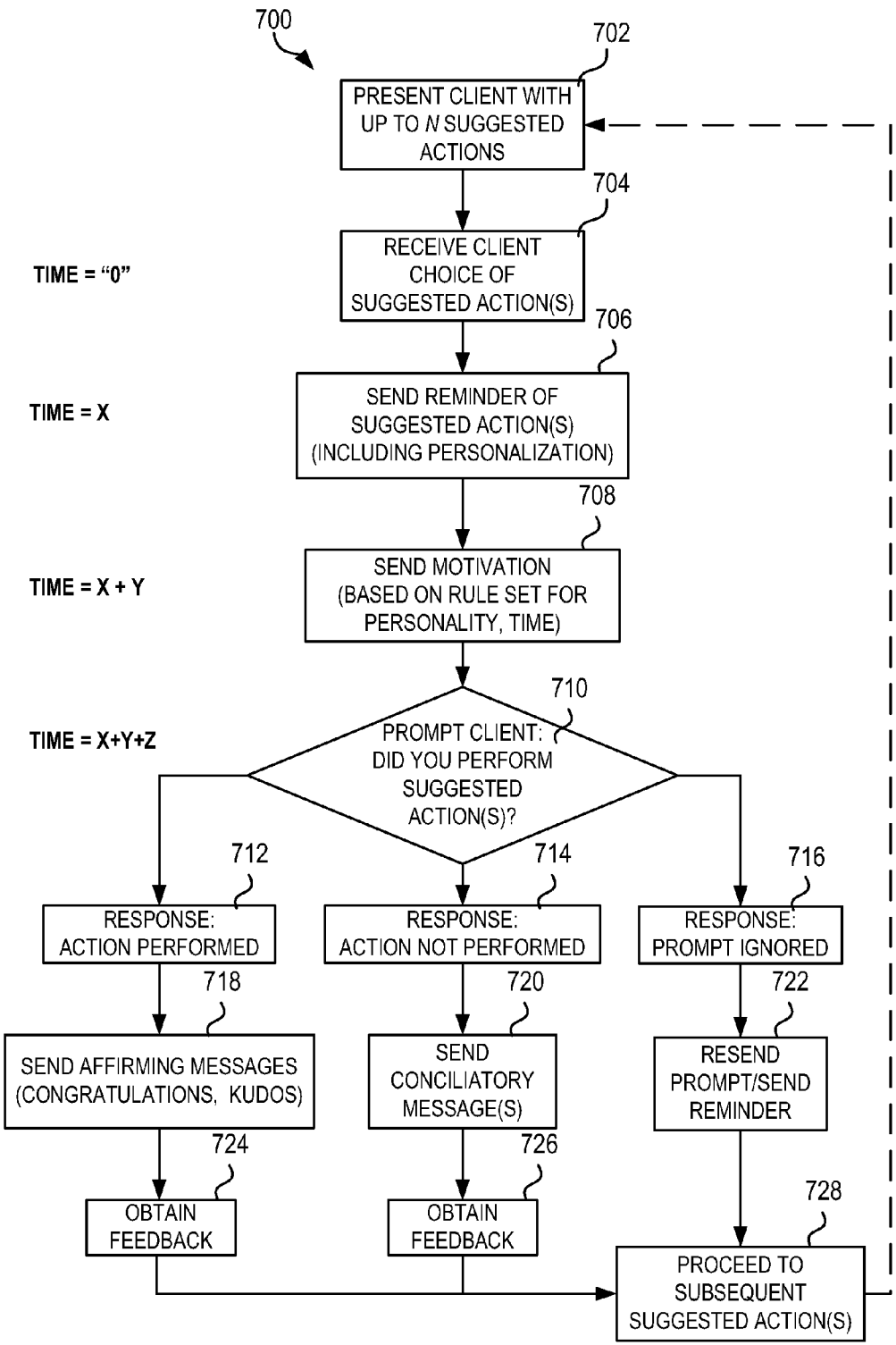
FIG. 7 illustrates an example technique of delivering suggested actions and obtaining feedback from human users, according to an example described herein.

The delivery, presentation, and response mechanisms for providing suggested content and suggested actions may be provided in a linear process to encourage action and appropriate feedback. FIG. 7 provides an illustration of a technique 700 for delivering suggested actions and obtaining feedback from human users according to an example.

At operation 702, a client 106 can be presented with up to N suggested actions. The suggested actions can be chosen using data processing technique 400, or filtering and weighting technique 500. At operation 704, the system can receive the client's choice of suggested action(s). At operation 706, the system can send a reminder to the client 106 that the chosen suggested action should be accomplished. At operation 708, a motivating message can be sent to the client 106. The motivating message can be configured as a function of the client's personality type 210, the goal(s) 204, the time frame which the client 106 set to accomplish the goal 204, or other data 208 or context information 406.

At operation 710, the system can prompt the client 106 to indicate whether they performed the chosen suggested action or not. There are at least three responses the client 106 can provide.

In one scenario, at operation 712, the client 106 can respond that the suggested action was performed. At operation 718, the system can send an affirming message (e.g., a congratulations or kudos) to the client. At operation 724, the system can obtain feedback from the client 106, such as by asking the client 106 questions about their experience in performing the suggested action.

In another scenario, at operation 714, the client 106 can respond that the suggested action was not performed. At operation 720, a conciliatory message can be sent to the client 106 from the system. At operation 726, the system can obtain feedback from the client 106, such as by asking why the suggested action was not completed.

In another scenario, at operation 716, the client 106 can respond by ignoring the prompt. At operation 722, the system can resend the prompt, send a reminder that the suggested action should be performed, or present a different set of suggested actions, such as at operation 704.

Regardless of the response received from the client 106, the system can proceed to present subsequent suggested actions at operation 728 (e.g., the process can start over at operation 702).

Figure 8:
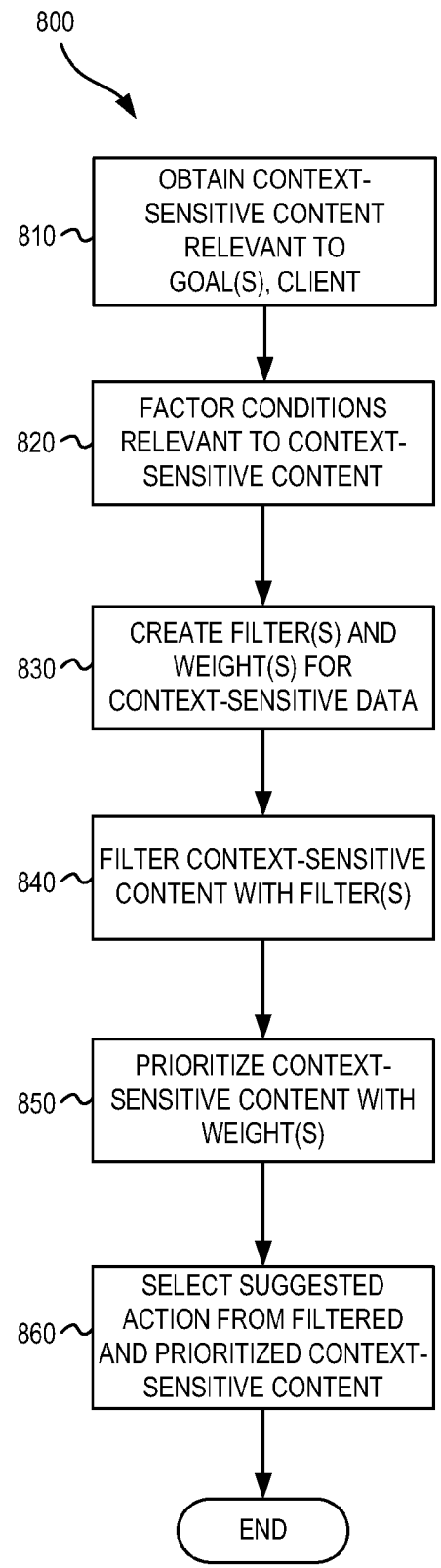
FIG. 8 illustrates an example method of determining suggested content from an information system, according to an example described herein.
Figure 9:
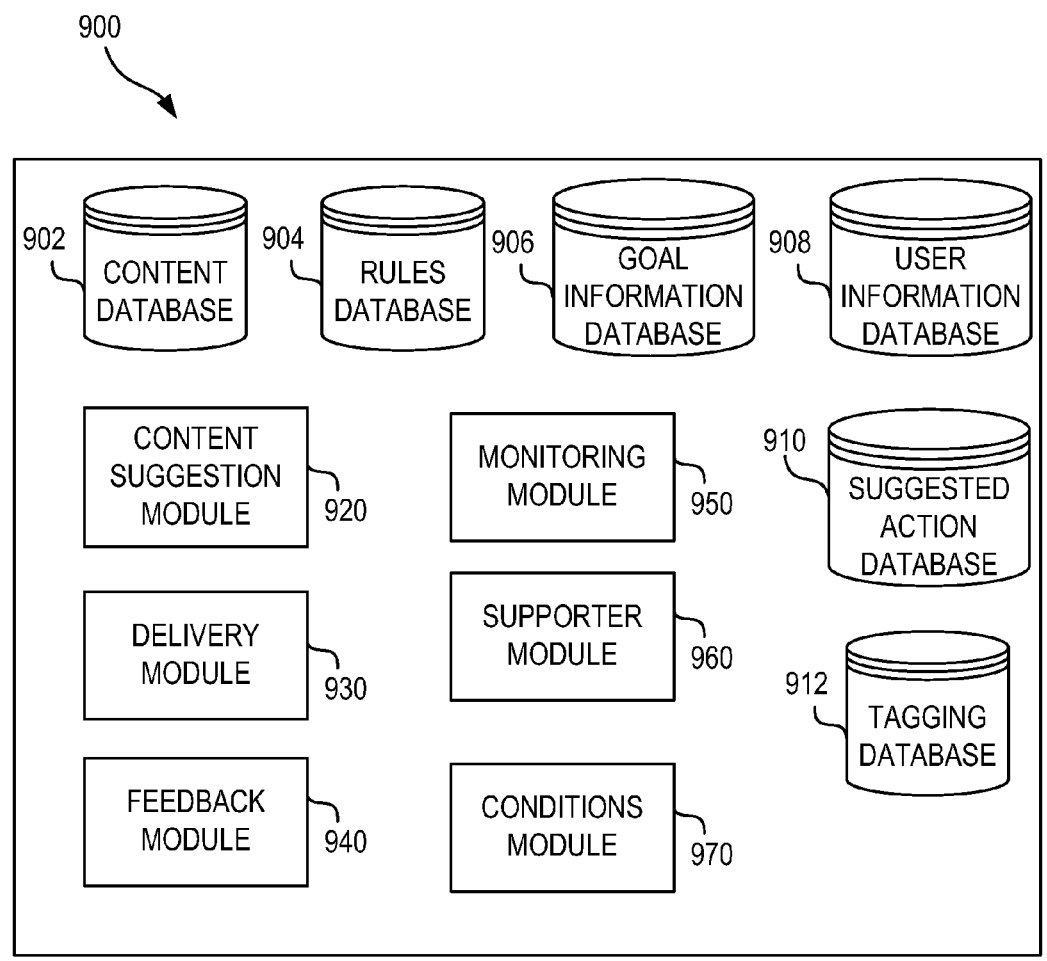
FIG. 9 illustrates an example system configuration of an information system arranged to provide suggested content, according to an example described herein.

FIG. 8 illustrates an example of a technique performed by a suggestion engine (e.g., content suggestion engine 102) for determining suggested content from an information system (e.g., information system 900 illustrated in FIG. 9).

At operation 810, context-sensitive content 408 can be obtained, such as described with regard to FIG. 4. The context-sensitive content 408 can be relevant to the client 106 (e.g., personality type 210, barriers 214, incentives 216, contextual information 218, data 208) and the goal(s) 204 of the client 106. At operation 820, conditions relevant to timing, delivery, access, subscription, or use of the context-sensitive content 408 can be factored (such as data conditions 108 specific to the client 106). At operation 830, filter(s) 410 and weight(s) 412 can be created. The filter(s) 410 and weight(s) 412 can be created as a function of the client's likes, dislikes, barriers 214, incentives 216, goal(s) 204, personality type 210, data 208, or a combination thereof, among others. At operation 840, the context-sensitive content 408 can be filtered, such as by filter(s) 410. At operation 850, the context-sensitive content 408 can be prioritized, such as by weight(s) 412. At operation 860, one or more suggested actions can be selected from the filtered (operation 840) and prioritized (operation 850) context-sensitive content 408.

Context-sensitive content 408 relative to a goal 204 can be experiential data (e.g., data learned through the client's interactions with the system). The client 106, the client's goal(s) 204, and the weighted and filtered context-sensitive content 408 can each include their own corresponding matrices. At least one suggested action message 302 to present to the client 106 can be selected through mathematical operations including these matrices, such as finding a minimum distance between matrices, multiplying, adding, subtracting, inverting, or performing other such operations on the matrices. Feedback received from the client 106 can be factored into a matrix so as to change the outcome of the mathematical operations and provide suggested actions that are better suited for the client 106 or the goal 204.

FIG. 9 illustrates an example of a system configuration of an information system 900 configured to provide content. The information system 900 can include a content database 902, a rules database 904, a goal information database 906, a user information database 908, a suggested action database 910, and a tagging database 912.

The content database 902 can include information from external sources, such as the supporter network 104, a professional expert working in a field relevant to a goal 204, other databases, or a combination thereof, among others. The rules database 904 can include rules for formatting and providing personalized suggested actions 302 to the client 106. Such rules can include timing restrictions, wording suggestions or restrictions, or suggested action restrictions (e.g., a suggested action message 302 with a certain tag should not be presented to a specific client 106).

The goal information database 906 can include data relevant to getting the client 106 to achieve a particular goal 204. The goal information can include certain activities that are useful to achieving a goal 204 (e.g., running a marathon requires the client to run to achieve the goal 204), recommended for achieving the goal 204 (e.g., stretching muscles and breathing exercises are helpful, but not essential, in training for a marathon), activities that are fun (e.g., things to keep the client 106 in a positive state of mind or reward the client 106 for their hard work or achievements), or a combination thereof, among others.

The user information database 908 can include information gained from questionnaires or learned through the client 106 or supporters in the supporter network 104 using the system. The user information database 908 can include information about all users of the system including supporters, clients 106, administrators of the system, or potential clients, among others. The suggested action database 910 can include suggested actions 302 including pre statements 304, action statements 306, and post statements 308. The suggested action database 904 can also include a record of which client has completed which suggested action 302, when the client 106 completed the suggested action 302, or how long it has been since the system recommend that suggested action 302 to the client 106. The tagging database 912 can include a record of all the tags and tagging relationships that have been created for suggested actions 302, playlists, or programs, and which suggested actions 302, programs, or playlists the tag is associated with.

While FIG. 9 shows six separate databases 902-912, the information contained within the databases may be contained within any number of databases. For example, the information in the suggested action and tagging databases 910, 912 can be combined into a single database.

The information system 900 can include one or more modules including a content suggestion module 920, a delivery module 930, a feedback module 940, a monitoring module 950, a supporter module 960, or a conditions module 970. The content suggestion module 920 can receive suggested actions 302 or have access to the suggested action database 910. The content suggestion module 920 can include the filter(s) 410 and the weight(s) 412, such as to allow the content suggestion module 920 to filter, prioritize, or present suggested actions 302 to the client 106.

The delivery module 930 can present at least one suggested action 302 or message to the supporter network 104 or the client 106, such as at a certain relevant time. The delivery module 930 can be configured to modify or amend the suggested action 302 or message that is delivered so as to be appropriate for the client 106. Such a configuration can make the client 106 more likely to complete the suggested action 302.

The feedback module 940 can be configured to receive feedback about suggested actions 302 from a client 106, process the feedback, and send the processed feedback to the user information database 908, rules database 904, content database 902, or suggested action database 904.

The monitoring module 950 can be configured to monitor a client's progress towards their goal(s) 204, a client's progress on completing a suggested action 302, program, or playlist, and can provide the delivery module 930 with information relevant to which messages (e.g., prompts, reminders, or encouragements) should be sent to the client 106.

The supporter module 960 can be configured to provide the supporter network 104 with the ability to make suggestions for a suggested action 302 to present to the client 106, provide information relevant to getting the client 106 to their goal 204 (e.g., likes, dislikes, barriers 214, or incentives 216 for the client 106, etc.), suggest messages to send to the client 106 that can be modified by the delivery module 930, or suggest tags that should be associated with the client 106.

The conditions module 970 can be configured to maintain relevant information from the ecosystem of conditions 212 and the client data conditions 108 that are relevant to the selection and delivery of relevant content. This may include direct or derived contextual data, or data relevant to barriers and incentives. For example, the contextual information maintained in conditions module may provide input for rules to express the conditions to deliver content to the proper user, at the proper time, in the proper context, and with the proper communication medium.

Computing System Architectures and Example Implementations

Figure 10:
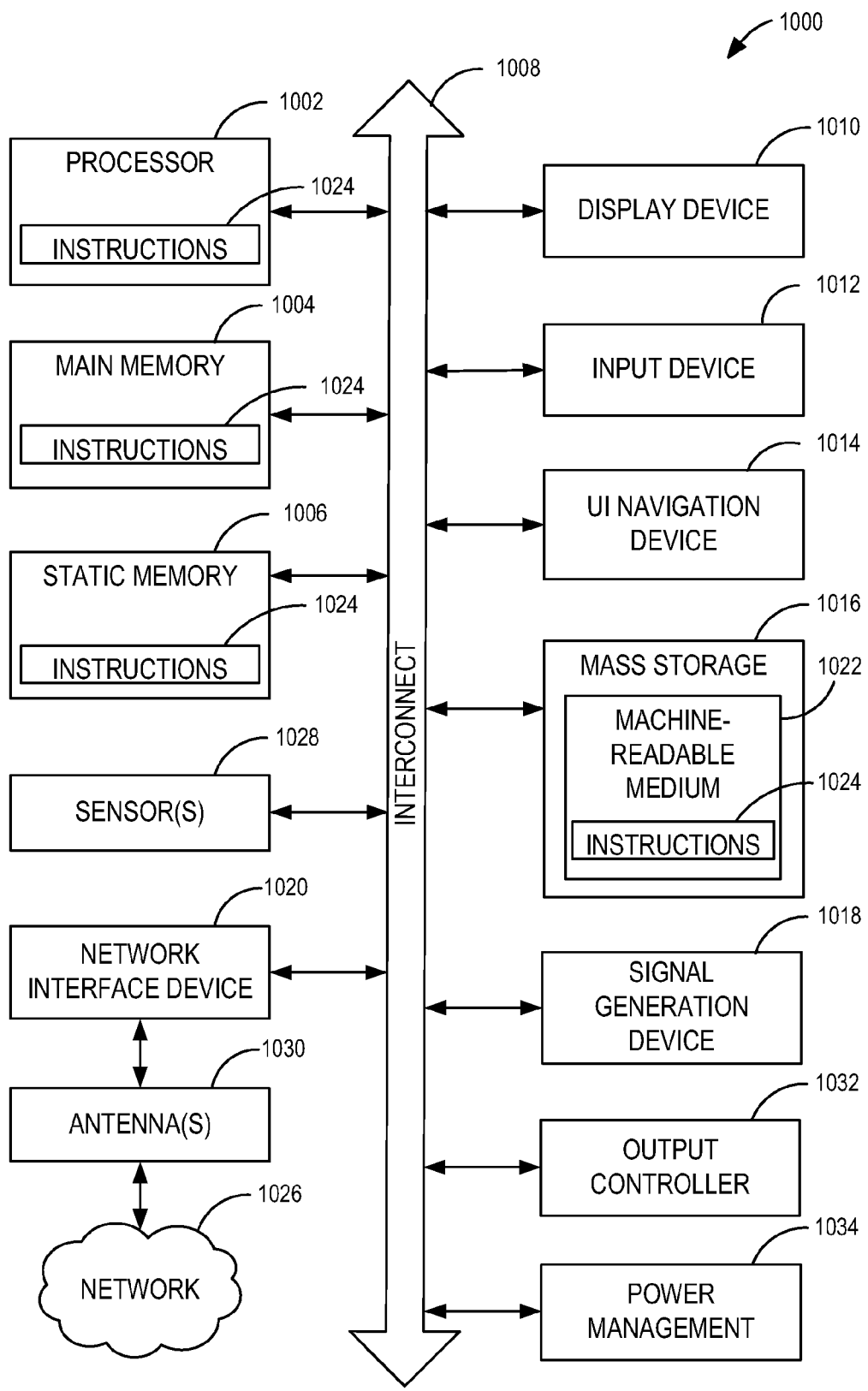
FIG. 10 illustrates an example of a computer system to implement techniques and system configurations, according to an example described herein.

FIG. 10 is a block diagram illustrating an example computer system machine upon which any one or more of the methodologies herein discussed may be run. Computer system 1000 may be embodied as a computing device, providing operations of the content suggestion engine 102 or information system 900 (from FIGS. 1 and 9), or any other processing or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a set-top box (STB), a gaming console, a personal digital assistant (PDA), a mobile telephone or smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1000 includes a processor 1002 (e.g., a central processing unit (CPU), a graphics processing unit (GPU) or both), a main memory 1004 and a static memory 1006, which communicate with each other via an interconnect 1008 (e.g., a link, a bus, etc.). The computer system 1000 may further include a video display unit 1010, an alphanumeric input device 1012 (e.g., a keyboard), and a user interface (UI) navigation device 1014 (e.g., a mouse). In one embodiment, the video display unit 1010, input device 1012 and UI navigation device 1014 are a touch screen display. The computer system 1000 may additionally include a storage device 1016 (e.g., a drive unit), a signal generation device 1018 (e.g., a speaker), an output controller 1032, a power management controller 1034, and a network interface device 1020 (which may include or operably communicate with one or more antennas 1030, transceivers, or other wireless communications hardware), and one or more sensors 1028, such as a global positioning sensor (GPS) sensor, compass, location sensor, accelerometer, or other sensor.

The storage device 1016 includes a machine-readable medium 1022 on which is stored one or more sets of data structures and instructions 1024 (e.g., software) embodying or utilized by any one or more of the methodologies or functions described herein. The instructions 1024 may also reside, completely or at least partially, within the main memory 1004, static memory 1006, and/or within the processor 1002 during execution thereof by the computer system 1000, with the main memory 1004, static memory 1006, and the processor 1002 also constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions 1024. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. For example, the suggestion engine 102 can include or be embodied on a server running an operating system with software running thereon. While some embodiments described herein illustrate only a single machine or device, the terms "system," "machine," or "device" shall also be taken to include any collection of machines or devices that individually or jointly execute a set (or multiple sets) of instructions to perform any one or more of the methodologies discussed herein.

Embodiments may also be implemented as instructions stored on a computer-readable storage device or storage medium, which may be read and executed by at least one processor to perform the operations described herein. A computer-readable storage device or storage medium may include any non-transitory mechanism for storing information in a form readable by a machine (e.g., a computer). For example, a computer-readable storage device or storage medium may include read-only memory (ROM), random-access memory (RAM), magnetic disk storage media, optical storage media, flash-memory devices, and other storage devices and media. In some embodiments, the electronic devices and computing systems described herein may include one or more processors and may be configured with instructions stored on a computer-readable storage device.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor may be configured as respective different modules at different times. Software may accordingly configure a hardware processor, for example, to constitute a particular module at one instance of time and to constitute a different module at a different instance of time.

Additional examples of the presently described method, system, and device embodiments include the following, non-limiting configurations. Each of the following non-limiting examples can stand on its own, or can be combined in any permutation or combination with any one or more of the other examples provided below or throughout the present disclosure.

Example 1 includes the subject matter as defined by a method performed by a computer-implemented content suggestion engine for determining suggested content from an information system, comprising: obtaining context-sensitive content relevant to attainment of an overall goal by a human subject, with the context-sensitive content produced from content data stored in an information system; applying a set of conditions relevant to the attainment of the overall goal to establish a filter and a weight for restricting the context-sensitive content, with the set of conditions including a psychological profile of the human subject, and the psychological profile tracking a psychological characteristic affecting the attainment of the overall goal by the human subject; filtering the context-sensitive content with the filter, to exclude content from the context-sensitive content; prioritizing the context-sensitive content with the weight, to prioritize content in the context-sensitive content; and selecting suggested content from the filtered and prioritized context-sensitive content for presentation to the human subject.

In Example 2, the subject matter of Example 1 can optionally include determining timing of delivery of the suggested content, based on the set of conditions relevant to the attainment of the overall goal; and electronically delivering the suggested content to the human subject according to the determined timing of delivery.

In Example 3, the subject matter of one or any combination of Examples 1-2 can optionally include the set of conditions relevant to the attainment of the overall goal including a plurality of conditions determined from creation of the psychological profile, the psychological profile being created from one or more of: input collected from the human subject, input collected from a human supporter of the human subject, a psychological model, or a coaching model; and wherein the context-sensitive content is further restricted to activities suggested by the context-sensitive content that match attributes of the psychological profile of the human subject.

In Example 4, the subject matter of one or any combination of Examples 1-4 can optionally include applying a set of conditions relevant to the context-sensitive data including: determining whether the context-sensitive content influences the human subject; determining whether the human subject influences the context-sensitive content; and, based on a determination of a relationship between the context-sensitive content and the human subject, modifying the filter and the weight.

In Example 5, the subject matter of one or any combination of Examples 1-4 can optionally include updating the context-sensitive content based on information obtained from the human subject.

In Example 6, the subject matter of one or any combination of Examples 1-5 can optionally include the information being obtained from the human subject by querying the human subject with one or more episodic questions.

In Example 7, the subject matter of one or any combination of Examples 1-6 can optionally include the suggested content indicating a suggested action for performance by the human subject, the suggested action being relevant to attainment of the overall goal by the human subject.

In Example 8, the subject matter of one or any combination of Examples 1-7 can optionally include prioritizing the context-sensitive content with the weight including prioritizing the context-sensitive content based on a plurality of weights, with respective of the plurality of weights having varying values.

In Example 9, the subject matter of one or any combination of Examples 1-8 can optionally include prioritizing the context-sensitive content with the weight including prioritizing the context-sensitive content as a function of the number of times the human subject has completed one or more suggested actions associated with a behavior change attribute, with the behavior change attribute relevant to one or more of: intrinsic motivation, extrinsic motivation, individual aptitude, group factors, group power, environmental factors, or environmental power to cause behavior change.

In Example 10, the subject matter of one or any combination of Examples 1-9 can optionally include prioritizing the context-sensitive content with the weight further including prioritizing the context-sensitive content associated with the behavior change attribute.

In Example 11, the subject matter of one or any combination of Examples 1-10 can optionally include the behavior change attribute being completed by the human subject a fewest number of times among a plurality of behavior change attributes for previous selections of context-sensitive content.

In Example 12, the subject matter of one or any combination of Examples 1-11 can optionally include applying a set of conditions relevant to the context-sensitive data including matching a difficulty tag of a suggested action from the context-sensitive content to a difficulty appropriate for the human subject.

Example 13 can include, or can optionally be combined with all or portions of the subject matter of one or any combination of Examples 1-12, to include the subject matter embodied by an information system, comprising: a content database storing content items; a content suggestion module implemented using a processor, with the content suggestion module configured for selection of suggested content from the context-sensitive content in the content database, and the context-sensitive content being relevant to attainment of an overall goal by a human subject, wherein to select the suggested content, the content suggestion module is configured to: establish a filter and a weight for narrowing the selection of context-sensitive content using a condition relevant to the attainment of the overall goal, with the condition including a psychological profile of the human subject; filter the context-sensitive content with the filter in order to exclude content from the context-sensitive content that does not satisfy the condition; and prioritize the context-sensitive content with the weight, to produce the selection of the suggested content from the context-sensitive content having a largest prioritization from the condition; and a content delivery module implemented using the processor, with the content delivery module configured to electronically provide the selection of the suggested content based on timing, and modify content of the selection of the suggested content to increase relevance to the human subject; wherein the selection of the suggested content includes one or more suggested actions for performance by the human subject, with the one or more suggested actions relevant to the attainment of the overall goal by the human subject.

In Example 14, the subject matter of Example 13 can optionally include the weight being used to provide a preference for content having an attribute associated with an incentive of the human subject, and wherein the filter is used to remove content having an attribute conflicting with a restriction of the human subject.

In Example 15, the subject matter of one or any combination of Examples 13-14 can optionally include the condition relevant to the attainment of the overall goal including a plurality of conditions determined from creation of the psychological profile, with the psychological profile created from one or more of: input collected from the human subject, input collected from a human supporter of the human subject, a psychological model, or a coaching model; and wherein the context-sensitive content is further filtered based on contextual impact of a plurality of activities being suggested to the human subject or to the overall goal by the suggested content.

In Example 16, the subject matter of one or any combination of Examples 13-15 can optionally include a supporter module configured to invoke interaction with one or more additional human supporters for attainment of the overall goal by the human subject, with the one or more additional human supporters connected in a social network with the human subject, and the supporter module operably coupled to the content delivery module to deliver at least part of the suggested content to the human subject through one or more interactions between the one or more additional human supporters and the human subject.

In Example 17, the subject matter of one or any combination of Examples 13-16 can optionally include a conditions module configured to evaluate the condition relevant to the attainment of the overall goal to select the selected content, the conditions including one or more of: a psychological profile of the human subject; a medical condition of the human subject; a lifestyle profile of the human subject; a demographic profile of the human subject; and a goal set for the human subject.

In Example 18, the subject matter of one or any combination of Examples 13-17 can optionally include a feedback module configured to receive feedback from the human subject about one or more suggested actions presented to the human subject from the suggested content.

In Example 18, the subject matter of one or any combination of Examples 12-17 can optionally include a monitoring module configured to monitor progress of the human subject toward at least one of: the overall goal, completion of a suggested action presented to the human subject from the suggested content, or completing a playlist of suggested actions presented to the human subject from the suggested content; wherein the monitoring module is further configured to monitor a response of the human subject to the suggested content.

In Example 20, the subject matter of one or any combination of Examples 13-19 can optionally include a rules database configured to maintain data for one or more rules used to filter and prioritize the context-sensitive content, and for one or more rules used to display the suggested content; a goal information database configured to maintain data for the overall goal by the human subject and one or more actions associated with attainment of the overall goal by the human subject; a tagging database configured to maintain data tag attributes for the context-sensitive content; and a suggested action database configured to maintain data for selected actions provided by the suggested content, and for responses by the human subject to the suggested content; wherein the content suggestion module is operably coupled to and accesses the rules database, the goal information database, the tagging database, and the suggested action database, in connection with the narrowing selection of the context-sensitive content.

Example 21 can include, or can optionally be combined with all or portions of the subject matter of one or any combination of Examples 1-20, to include the subject matter embodied by a machine readable storage medium comprising a plurality of instructions that, in response to being executed on a computing device, cause the computing device to: retrieve, from content data stored in an information system, context-sensitive content relevant to attainment of an overall goal by a human subject; establish one or more restrictions and one or more preferences for the context-sensitive content from a set of conditions relevant to the attainment of the overall goal, the set of conditions including a psychological profile of the human subject, and the psychological profile tracking a psychological characteristic affecting the attainment of the overall goal by the human subject; filter the context-sensitive content using at least one of the one or more restrictions to exclude content from the context-sensitive content; prioritize the context-sensitive content with the one or more preferences to prefer content from the context-sensitive content; and produce suggested content from the filtered and prioritized context-sensitive content for presentation to the human subject.

In Example 22, the subject matter of Example 21 can optionally include instructions, which when executed by the computing device, cause the computing device to: determine timing of delivery of the suggested content; and deliver the suggested content to the human subject according to the determined timing of delivery.

In Example 23, the subject matter of one or any combination of Examples 21-22 can optionally include the set of conditions relevant to the context-sensitive data including conditions determined from one or more of: input from the human subject, input from a human supporter of a human subject, or a coaching model; and wherein the context-sensitive data impacts or is impacted by the human subject or the environmental goal.

In Example 24, the subject matter of one or any combination of Examples 21-23 can optionally include the instructions for applying a set of conditions relevant to the context-sensitive data include instructions, which when executed by the computing device, cause the computing device to: determine whether the context-sensitive data influences the subject; determine whether the human subject influences the context-sensitive data; determine whether the human subject and the context-sensitive data are independent of each other; and modify the filter and the weight based on a determination of a relationship between the context-sensitive data and the human subject.

In Example 25, the subject matter of one or any combination of Examples 21-24 can optionally include instructions, which when executed by the computing device, cause the computing device to update the context-sensitive data based on information obtained from the human subject.

In Example 26, the subject matter of one or any combination of Examples 21-25 can optionally include instructions, which when executed by the computing device, cause the computing device to obtain the information from the human subject by querying the human subject with episodic questions.

In Example 27, the subject matter of one or any combination of Examples 21-26 can optionally include the instructions for prioritizing the context-sensitive content based on a weight that includes instructions, which when executed by the computing device, causes the computing device to prioritize the context-sensitive content based on a plurality of weights, with respective of the plurality of weights having varying values.

In Example 28, the subject matter of one or any combination of Examples 21-27 can optionally include the instructions for prioritizing context-sensitive content based on a weight including instructions, which when executed by the computing device, cause the computing device to prioritize the context-sensitive as a function of the number of times the human subject has completed suggested actions in a behavior change category.

In Example 29, the subject matter of one or any combination of Examples 21-28 can optionally include the instructions for applying a set of conditions relevant to the context-sensitive data including instructions, which when executed by the computing device, cause the computing device to match a difficulty tag of a suggested action of the plurality of suggested actions to a difficulty appropriate for the human subject.

The following claims are hereby incorporated into the detailed description, with each claim and identified combination of claims standing on its own as a separate example.

What is claimed is:

1. A non-transitory machine readable storage medium comprising a plurality of instructions for determining suggested content that, in response to being executed on a computing device, cause the computing device to:
    evaluate data that represents a plurality of personality and psychological characteristics of a human user, the data being obtained from a user information system, and the personality and psychological characteristics being relevant to an attainment of an overall health goal for the human user;
    evaluate data that represents a plurality of behaviors and actions of the human user, the data being obtained from the user information system, and the behaviors and actions being relevant to the attainment of the overall health goal for the human user;
    select a candidate set of context-sensitive content suggestions for the human user, the context-sensitive content suggestions being selected from a content information system, and the context-sensitive content suggestions indicating respective suggested actions for performance by the human user that assist the attainment of the overall health goal for the human user;
    filter the candidate set of context-sensitive content suggestions for the human user, based on matching the candidate set to the behaviors and actions of the human user, and matching the candidate set to the personality and psychological characteristics of the human user;
    prioritize a selected content suggestion from the candidate set of context-sensitive content suggestions for presentation to the human user, based on matching the selected content suggestion to the behavior and actions of the human user, and matching the selected content suggestion to a current state of the human user; and
    transmit data indicating the selected content suggestion, to cause display of the selected content suggestion to the human user in a graphical user interface of an electronic device.

2. The machine readable storage medium of claim 1, the instructions further to cause the computing device to:
    determine a time of presentation of the selected content suggestion to the human user in the graphical user interface, based on the current state of the human user;
    cause transmission of the selected content suggestion to an electronic device of the human user, to enable display of the selected content suggestion at the time of presentation.

3. The machine readable storage medium of claim 1, the instructions further to cause the computing device to:
    determine a preferred delivery location of the selected content suggestion, based on the current state of the human user and based on the personality and psychological characteristics of the human user; and cause transmission of the selected content suggestion to the preferred delivery location for presentation in the graphical user interface.

4. The machine readable storage medium of claim 1, the instructions further to cause the computing device to:
determine the current state of the human user, using one or more episodic questions; and
cause the selected content suggestion to be displayed to the human user in the graphical user interface in response to the one or more episodic questions.

5. The machine readable storage medium of claim 1, the instructions further to cause the computing device to:
obtain the data that represents the plurality of personality and psychological characteristics of a human user from a profile maintained in the user information system, the profile being created from one or more of: input collected from the human user, input collected from a human supporter of the human user, input collected from a human expert coach of the human user, a psychological model, or a coaching model.

6. The machine readable storage medium of claim 1, the instructions further to cause the computing device to:
obtain the data that represents the plurality of behaviors and actions of the human user from data captured by a wearable monitoring device, the wearable monitoring device being worn by the human user and capturing physiological and activity data of the human user.

7. The machine readable storage medium of claim 1, the instructions further to cause the computing device to:
filter the candidate set of context-sensitive content suggestions using one or more restrictions of the human user to exclude a first type of content; and
prioritize the selected content suggestion using one or more preferences of the human user to prefer a second type of content.

8. The machine readable storage medium of claim 7, the instructions further to cause the computing device to:
further prioritize the selected content suggestion based on application of a plurality of weights, the plurality of weights having varying values;
wherein operations to prioritize the selected content suggestion cause prioritization of the selected content suggestion as a function of a number of times the human user has completed one or more suggested actions associated with a behavior change attribute, the behavior change attribute relevant to one or more of: intrinsic motivation, extrinsic motivation, individual aptitude, group factors, group power, environmental factors, or environmental power to cause behavior change, wherein the suggested content suggestion is associated with the behavior change attribute.

9. The machine readable storage medium of claim 1, the instructions further to cause the computing device to:
further prioritize the selected content suggestion based on matches of a difficulty level suitable for the human user with an attribute of the selected content suggestion indicating a difficulty that is appropriate for the human user.

10. The machine readable storage medium of claim 1, wherein the overall health goal for the human user relates to: a scheduled administration of medicine, a chronic illness health condition, a long term care health condition, or a physical therapy treatment.

11. A method performed by a computer-implemented content suggestion engine for determining suggested content, comprising:
evaluating data that represents a plurality of personality and psychological characteristics of a human user, the data being obtained from a user information system, and the personality and psychological characteristics being relevant to an attainment of an overall health goal for the human user;
evaluating data that represents a plurality of behaviors and actions of the human user, the data being obtained from the user information system, and the behaviors and actions being relevant to the attainment of the overall health goal for the human user;
retrieving, from a content information system, a superset of context-sensitive content suggestions relevant to attainment of the overall health goal for the human user, the context-sensitive content suggestions indicating respective suggested actions for performance by the human user that assist the attainment of the overall health goal;
selecting a candidate set of context-sensitive content suggestions for the human user, the candidate set of context-sensitive content suggestions being selected from the superset of context-sensitive content suggestions;
filtering the candidate set of context-sensitive content suggestions for the human user, based on matching the candidate set to the behaviors and actions of the human user, and matching the candidate set to the personality and psychological characteristics of the human user;
prioritizing a selected content suggestion from the candidate set of context-sensitive content suggestions for presentation to the human user, based on matching the selected content suggestion to the behavior and actions of the human user, and matching the selected content suggestion to a current state of the human user.

12. The method of claim 11, further comprising:
determining a time of presentation of the selected content suggestion to the human user;
determining a delivery location of the selected content suggestion, based on the personality and psychological characteristics of the human user; and
electronically transmitting the selected content suggestion, to enable display of the selected content suggestion at the time of presentation and the delivery location.

13. The method of claim 11, further comprising:
collecting input from the human user using one or more episodic questions; and
presenting the selected content suggestion in a display that occurs in response to the one or more episodic questions.

14. The method of claim 13, further comprising:
updating the candidate set of context-sensitive content suggestions based on information obtained from the human user in response to the one or more episodic questions.

15. The method of claim 11, further comprising:
analyzing the plurality of personality and psychological characteristics of the human user from a profile, the profile including data from one or more of: input collected from the human user, input collected from a human supporter of the human user, input collected from a human expert coach of the human user, a psychological model, or a coaching model.

16. The method of claim 11, further comprising:
analyzing the plurality of behaviors and actions of the human user from a data of a wearable monitoring device, the wearable monitoring device being worn by the human user and capturing physiological and activity data.

17. The method of claim 11, further comprising:
filtering the candidate set of context-sensitive content suggestions using one or more restrictions of the human user to exclude a first type of content; and
prioritizing the selected content suggestion using one or more preferences of the human user to prefer a second type of content.

18. The method of claim 11, further comprising:
further prioritizing the selected content suggestion based on application of a plurality of weights, the plurality of weights having varying values;
wherein prioritizing the selected content suggestion includes prioritizing the selected content suggestion as a function of a number of times the human user has completed one or more suggested actions associated with a behavior change attribute, the behavior change attribute relevant to one or more of: intrinsic motivation, extrinsic motivation, individual aptitude, group factors, group power, environmental factors, or environmental power to cause behavior change, wherein the suggested content suggestion is associated with the behavior change attribute.

19. The method of claim 11, further comprising:
further prioritizing the selected content suggestion based on matches of a difficulty level suitable for the human user with an attribute of the selected content suggestion indicating a difficulty that is appropriate for the human user.

20. The method of claim 11, further comprising:
transmitting data indicating the selected content suggestion to an electronic device of the human user, to cause display of the selected content suggestion to the human user in a playlist of a plurality of content suggestions provided in a graphical user interface of an electronic device.

21. The method of claim 11, wherein the overall health goal for the human user relates to: a scheduled administration of medicine, a chronic illness health condition, a long term care health condition, or a physical therapy treatment.

22. An information system, comprising a computer system having at least one hardware processor, at least one memory, and at least one storage medium, the computer system configured to execute instructions from the at least one storage medium using the hardware processor and the memory, to cause the computer to:
evaluate data that indicates a plurality of personality and psychological characteristics of a human user, the personality and psychological characteristics being relevant to an attainment of an overall health goal for the human user;
evaluate data that indicates a plurality of behaviors and actions of the human user, the behaviors and actions being relevant to the attainment of the overall health goal for the human user;
select a candidate set of context-sensitive content suggestions for the human user, the context-sensitive content suggestions being relevant to the attainment of the overall health goal for the human user;
filter the candidate set of context-sensitive content suggestions for the human user, based on matching the candidate set to the behaviors and actions of the human user, and matching the candidate set to the personality and psychological characteristics of the human user;
prioritize a selected content suggestion from the candidate set of context-sensitive content suggestions for presentation to the human user, based on matching the selected content suggestion to the behavior and actions of the human user, and matching the selected content suggestion to a current state of the human user; and
generate data indicating the selected content suggestion for display to the human user in a graphical user interface.

23. The information system of claim 22, the computer system configured to execute further instructions from the at least one storage medium using the hardware processor and the memory, to cause the computer to:
determine a timing of the display to the human user;
determine a delivery location of the display to the human user; and
implement a modification to the suggested content to increase relevance to the human user.

24. The information system of claim 22, the computer system configured to execute further instructions from the at least one storage medium using the hardware processor and the memory, to cause the computer to:
evaluate a profile relevant to the attainment of the overall goal to prioritize the selected content suggestion, the profile including characteristics from one or more of: a psychological profile of the human user, a medical profile of the human user, a lifestyle profile of the human user, a demographic profile of the human user, or a goal set for the human user.

25. The information system of claim 22, the computer system configured to execute further instructions from the at least one storage medium using the hardware processor and the memory, to cause the computer to:
evaluate the plurality of personality and psychological characteristics of the human user using data from one or more of: input collected from the human user, input collected from a human supporter of the human user, input collected from a human expert coach of the human user, a psychological model, or a coaching model.

26. The information system of claim 22, the computer system configured to execute further instructions from the at least one storage medium using the hardware processor and the memory, to cause the computer to:
monitor progress of the human user toward at least one of: the overall goal, completion of a suggested action presented to the human user from the selected content suggestion, or completion of a playlist of suggested actions presented to the human user including the suggested action from the selected content suggestion;
receive feedback from the human user about the suggested action presented to the human user; and
monitor activity of the human user in response to the selected action.

27. The information system of claim 22, the computer system configured to execute further instructions from the at least one storage medium using the hardware processor and the memory, to cause the computer to:
suggest interaction with one or more additional human supporters for attainment of the overall goal by the human user, the one or more additional human supporters connected in a social network with the human user; and
cause delivery of at least part of the suggested content to the human user through one or more interactions between the one or more additional human supporters and the human user.

28. The information system of claim 22, further comprising:
- a content database maintained on the at least one storage medium, the content database configured to store the context-sensitive content suggestions;
- an attribute database maintained on the at least one storage medium, the attribute database configured to maintain attributes for the context-sensitive content suggestions; and
- a selection database configured to maintain data for one or more rules and one or more weights used to filter and prioritize the selected content suggestion from the context-sensitive content suggestions;
- wherein the computer system is operably coupled to and accesses the content database, attribute database, and selection database, in connection with selection of the selected content suggestion.

\* \* \* \* \*